United States Patent [19]
Meador

[11] Patent Number: 5,601,191
[45] Date of Patent: *Feb. 11, 1997

[54] LIQUID SPECIMEN VESSEL

[75] Inventor: James W. Meador, Houston, Tex.

[73] Assignee: KVM Technologies, Inc., Houston, Tex.

[*] Notice: The term of this patent shall not extend beyond the expiration date of Pat. No. 5,409,117.

[21] Appl. No.: 421,555

[22] Filed: Apr. 13, 1995

Related U.S. Application Data

[63] Continuation-in-part of Ser. No. 227,040, Apr. 13, 1994, Pat. No. 5,409,117.

[51] Int. Cl.$^6$ ............................................. A61M 1/00
[52] U.S. Cl. ......................... 206/569; 422/61; 422/102
[58] Field of Search ............................ 206/569, 570, 206/438; 128/760, 762, 766, 767; 604/317, 407; 422/61, 102, 104

[56] References Cited

U.S. PATENT DOCUMENTS

| | | | |
|---|---|---|---|
| 2,689,566 | 9/1954 | Lockhart . | |
| 2,793,776 | 5/1957 | Lipari . | |
| 4,221,295 | 9/1980 | Tuchband et al. | 206/569 |
| 4,315,570 | 2/1982 | Silver et al. | 206/221 |
| 4,408,905 | 10/1983 | Ehrenkranz . | |
| 4,458,811 | 7/1984 | Wilkinson | 206/219 |
| 4,512,471 | 4/1985 | Kaster et al. | 206/438 |
| 4,549,655 | 10/1985 | Forsythe, Jr. et al. | 206/569 |
| 4,589,548 | 5/1986 | Fay | 206/569 X |
| 4,761,379 | 8/1988 | Williams et al. | 435/296 |
| 4,769,215 | 9/1988 | Ehrenkranz . | |
| 4,852,560 | 8/1989 | Herman, Jr. et al. | 128/762 |
| 4,936,446 | 6/1990 | Lataix | 206/221 |
| 4,961,432 | 10/1990 | Guirguis | 128/760 |
| 4,981,144 | 1/1991 | Carels, Jr. | 128/760 |
| 4,986,322 | 1/1991 | Chibret et al. | 141/319 |
| 5,084,041 | 1/1992 | Oxley et al. | 604/410 |
| 5,088,627 | 2/1992 | Musel | 222/145 |
| 5,133,703 | 7/1992 | Boehringer et al. | 604/317 |
| 5,137,031 | 8/1992 | Guirguis | 128/762 X |
| 5,160,329 | 11/1992 | Oxley | 604/317 |
| 5,186,900 | 2/1993 | Jensen et al. | 422/104 |
| 5,217,443 | 6/1993 | Oxley | 604/317 |
| 5,353,961 | 10/1994 | Debush | 222/94 |
| 5,380,289 | 1/1995 | Hemstreet | 604/317 |
| 5,409,117 | 4/1995 | Meador | 206/569 |
| 5,423,792 | 7/1995 | Oxley | 604/409 |

*Primary Examiner*—Jacob K. Ackun
*Attorney, Agent, or Firm*—Tim L. Burgess

[57] ABSTRACT

A liquid vessel provides a means of assuring uncontaminated, multiple specimens of a liquid. Two containers are connected side-by-side by a retainer which accepts an optional detachable funnel assembly that directs liquid into each container. The retainer includes both a flexible serpentine connector loosely connecting collar portions of the retainer fitted to each container and a rigid portion fixing the spacing of the containers. Each container includes a sidewall flexure, and when the funnel is removed, each is closed by a closure that includes another sidewall flexure, a nozzle facing away from and basally open to the floor of the container, and a stiff basal projection extending to the floor of the container. Coupling members on the floor underside of the containers enable coupling of the floors of the two containers after the rigid portion of the retainer is severed. Pushing the closure of one of the containers reduces intra-chamber pressure in that container. The reduced pressure prevents discharge of specimen from the one container when a nozzle in the closure of that container is opened. Compressing the volume of the container with the opened nozzle discharges an aliquot of specimen from that container through the opened nozzle.

34 Claims, 19 Drawing Sheets

LIQUID SPECIMEN VESSEL

CROSS REFERENCE TO RELATED APPLICATION

This is a continuation-in-part of prior U.S. application Ser. No. 08/227,040, filed Apr. 13, 1994, now U.S. Pat. No. 5,409,117 the contents of which are incorporated herein by reference thereto.

FIELD OF THE INVENTION

The present invention relates generally to the field of liquid sampling and testing and more particularly to a urine specimen vessel that provides for redundant isolated specimens.

BACKGROUND

In fields such as clinical medicine, forensic sciences, environmental quality testing, food quality assurance, drug testing, and other areas, it has become possible to determine the presence and/or amount of trace substances in test samples even when such substances are present in very low concentrations (on the order of parts per million, or even per billion). For example, during testing of urine, it is now possible to detect and quantify trace quantities of most known illicit drugs. Further, as a result of such drug testing, positive test results may have a profound impact on the donor's career or employment. In the proper circumstances, positive test results may also result in criminal liability for the donor.

Such circumstances dictate that the security or chain-of-custody of the specimen be preserved and that any tampering of the specimen be immediately apparent. It is desirable that test results be verifiable by repeating the tests on an identical specimen. It is also important that the specimen be capable of being "split", in order that a secure portion of the specimen can be sent to another laboratory for independent confirmation of the test results.

Similarly, other liquid sampling procedures present the same issues of repeatability and integrity verifiability. For example, the U.S. Environmental Protection Agency conducts a variety of ongoing testing programs. These testing programs are intended to guarantee compliance with standards for maximum levels of toxic and/or radioactively contaminated liquids, such as plant effluent. In the event of a test indicating non-compliance with such a standard, it is important that the EPA be able to repeat the test on another, identical specimen. It is equally important that the EPA be able to verify that the specimen that is tested is indeed the specimen that was taken and that no foreign substances have been introduced into the specimen without being tamper evident.

Thus, there remains a need for a liquid specimen vessel that provides for more than one isolated specimen of a sample. Such a vessel should provide for splitting of the specimen for independent testing. The vessel should also minimize or even eliminate the possibility of contamination of the test specimen. Further, the vessel should automatically retain an archival specimen so that any tests may be repeated on an identical test specimen and the results of the tests verified. Such a specimen vessel should be easy to use and simple in construction. It should also present a geometric aspect that is sufficiently simple to be easily moldable by known molding techniques.

SUMMARY OF THE INVENTION

The present invention provides these and other features of a vessel for a liquid specimen, and gives a novel method of sampling a liquid specimen. The invention involves a vessel in which a liquid to be tested is placed. The vessel comprises a container and a closure for the container. The container and the closure each contain a sidewall having a linear expansion portion which can be expanded and retracted or compressed to provide an enlargement or reduction of the included volume of the container. The closure has a member which projects toward the floor of the container when the container is closed with the closure, and also has a nozzle which projects away from the floor of the closed container. The nozzle is open only to the interior of the closed container. This structure of container and closure permits manipulation and elongation of either or both of the container and closure to create reduced pressure inside the closed container when it contains a liquid, after which an aperture can be created in the nozzle projection to permit pressure within the container to equilibrate with ambient pressure without expulsion of liquid through the aperture. The container or closure or both then can be manipulated to expel liquid from the container for assay.

To provide a separate isolated specimen in accordance with the invention, two of the containers and closures are interconnected by a retainer, of which at least one portion fixes the containers side-by-side for ease of specimen filling and the other loosely ties together the two containers. After collection of the specimen in each of the two containers, the portion fixing the two tied containers is severed. The two loosely tied containers may then be coupled "foot-to-foot" by mating connectors located on the underside of the floor of each container. The specimen may then be obtained from the "head-down" or inverted container, leaving the other (upright) container unaccessed. The tie connecting the unaccessed container may then be severed, and the unaccessed container placed in storage for follow-up verification if needed. Alternatively, the tie loosely connecting the two containers may be severed at the same time the retainer fixing portion is severed, and one of the two containers put aside for reserve while the other is accessed for testing of the liquid contained therewithin.

Thus, this invention is directed to a liquid vessel comprising a container including a stiff floor, a sidewall connected at a lower portion of the sidewall to the floor and having an upper portion including an opening into the container. Below the upper portion of the sidewall, the sidewall includes a linear expansion or flexure portion. A closure is provided for the container. The closure includes a stiff base smaller than the container opening and a closure sidewall connected at a lower portion thereof to the base. The closure sidewall further includes a linear expansion or flexure portion. The closure base has a topside and a bottomside. The bottomside includes a dependent stiff projection of length to extend adjacent the container floor upon closure of the container, and the topside includes at least one upstanding nozzle opening only to the bottomside.

To provide a separate isolated specimen in accordance with this invention, two of the containers and closures are interconnected by a retainer, of which at least one portion fixes the containers horizontally side-by-side and another portion loosely connects the two containers.

To facilitate filling the two interconnected containers, the invention further comprises a connectable funnel. The funnel includes a wall tapering inwardly from an upper entrance opening to two lower outlets positioned below the funnel opening, the funnel between the entrance opening and the outlets having a distributor for distributing to both the outlets a liquid admitted through the funnel entrance opening. For the connection of the funnel, the retainer interconnecting the two containers includes one member of at least one pair of companion means for releasably connecting the funnel to the retainer in position to empty liquid from the funnel outlets into the container openings in the absence of the container closures. The funnel has the other member of the at least one companion means. This other member is located exteriorly of the funnel wall for releasable connection of the funnel to the retainer.

The configuration of the vessel providing these mechanisms is advantageous in that it lends itself to being easily moldable and adaptable for machine manipulation for automated sampling.

The novel methods of sampling the vessel of this invention will be better understood and is set forth after the description of the embodiments of the vessel and vessel assemblies which follows.

These and other features of the present invention will be apparent to those of skill in the art from the following detailed description in conjunction with the drawings.

DETAILED DESCRIPTION OF PREFERRED EMBODIMENTS

Figure 1:
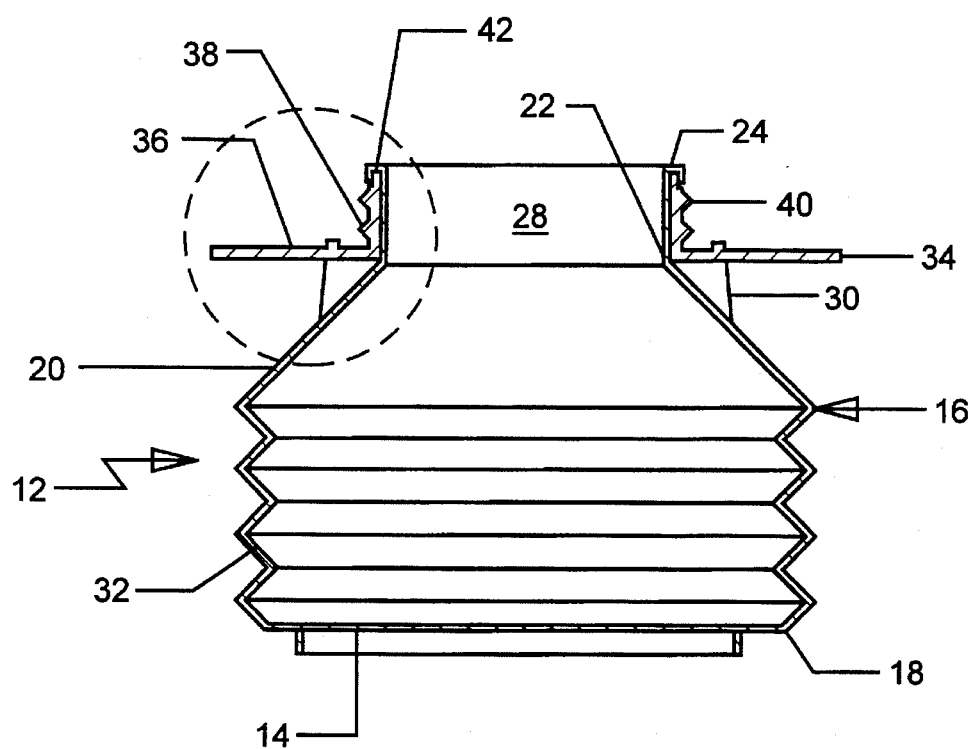
FIG. 1 is a schematic side vertical sectional view of a container and collar portion of a retainer in an embodiment of a vessel of this invention.

Referring to FIG. 1, a vessel 10 comprises a container 12 including a stiff floor 14 having an upperside 15, a sidewall 16 connected at a lower portion 18 thereof to floor 14 and having an upper portion 20 tapering inwardly to a neck 22 including a rim 24 surrounding an opening or throat 28 into the interior of container 12. A retainer stop 30 is formed on the exterior circumference of taper 22. Sidewall 16 includes a linear expansion or flexure portion 32 below upper portion 20. Sidewall flexure portion 32 suitably is a bellows or accordion-like structure in which concentric rings or pleats are molded as a linear expansion element. The expansion element may also take the form of a single or multi-ring spiral.

Figure 2:
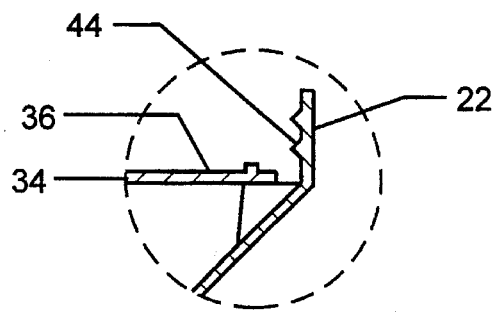
FIG. 2 is schematic side vertical sectional view of an alternative embodiment of a portion of the container and retainer portion of FIG. 1.

Container 12 further includes means on the container for coacting with a closure for sealingly securing the closure to the container. Surrounding container neck 22 is a retainer 34 with a collar portion 36 supported by retainer stop 30. Collar portion 36 in the embodiment depicted in FIG. 1 includes an upright portion suitably barrel 38 surrounding an upper portion of the container between the rim 24 and the container flexure portion 32, suitably at neck 22 of container 12. Collar barrel 38 has screw threads 40 formed on the exterior thereof. In this embodiment, container neck 22 is fabricated of a material that is relatively deformable and rim 24 forms a gasket supported by the upper barrel 42 of barrel 38. In an alternative embodiment shown in FIG. 2, container neck 22 is rigid and has screw threads 44 formed on its exterior. In this latter embodiment, retainer 34 has no barrel portion 38.

Figure 3:
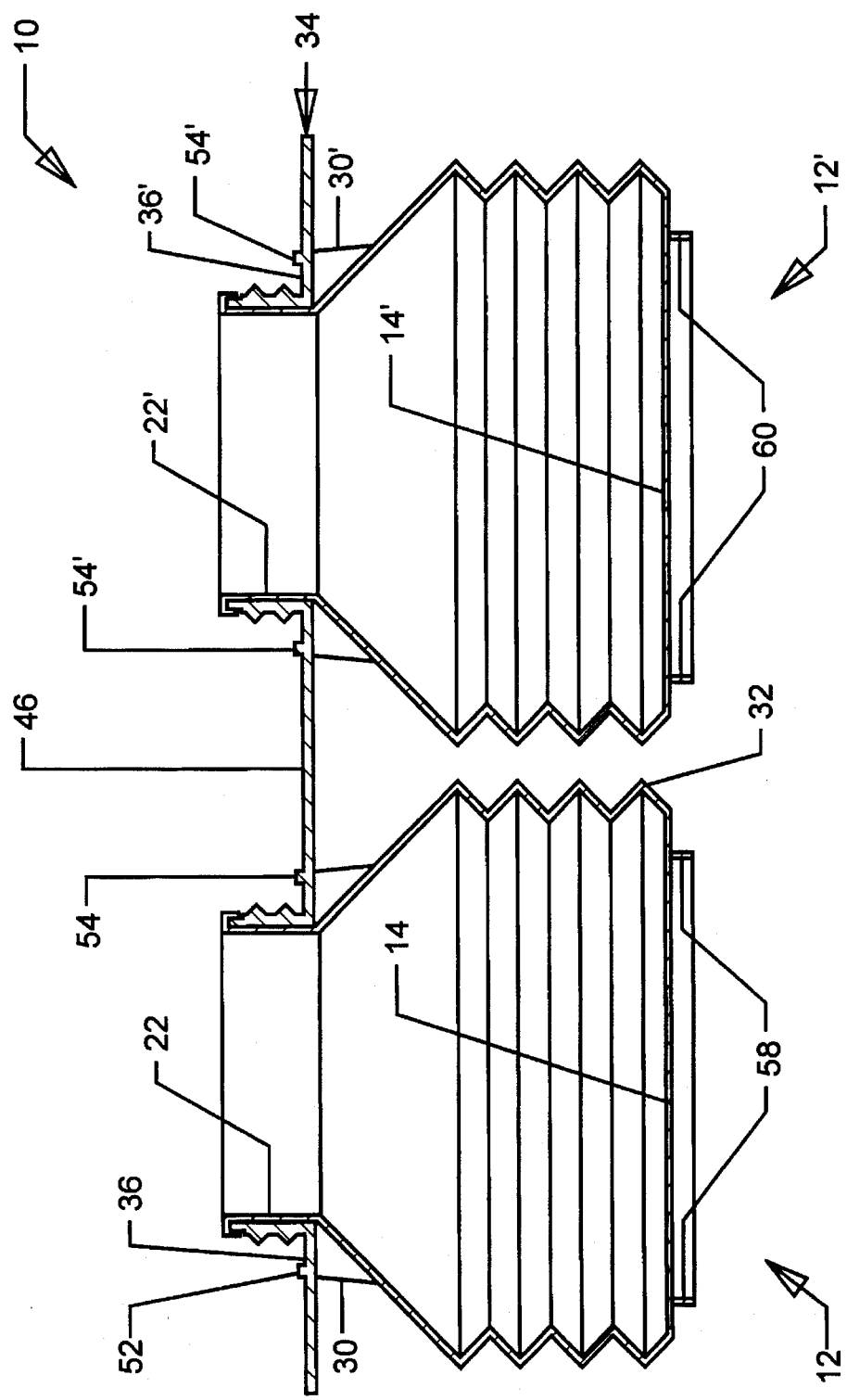
FIG. 3 is a schematic side vertical sectional view of two containers fixedly joined by a retainer of a vessel of this invention.
Figure 4:
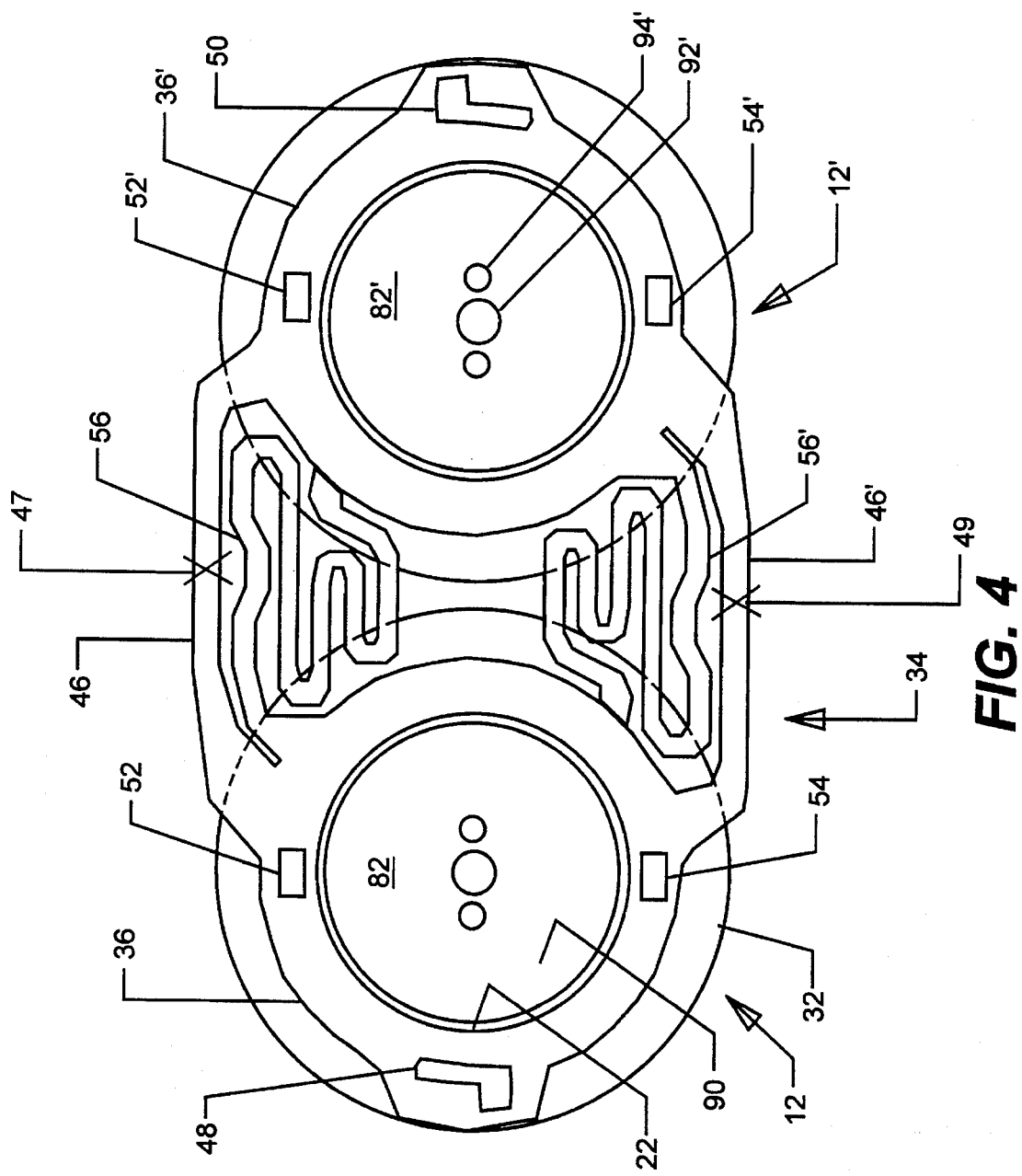
FIG. 4 is a schematic top plan view of the two joined containers of FIG. 3.

Referring to FIG. 3, retainer 34 fixingly connects two containers 12 and 12' horizontally side-by-side. (In FIG. 3 and in subsequent figures, a prime symbol (') appended to an Arabic numeral indicates an element or structure in container 12' corresponding to the like element or structure indicated by the same Arabic numeral in container 12.) Referring to FIG. 4, retainer 34 comprises collar portions 36 and 36', rigid portions 46 and 46' fixedly connecting the two containers 12 and 12'. Retainer 34 also comprises flexible serpentine connector or tie portions 56 and 56' loosely connecting collar portions 36 and 36'. Collar portions 36 and 36' are fitted over necks 22 and 22' of containers 12 and 12' as shown in FIGS. 1 (or 2) and 3. Collar portions 36 and 36' each include one member of at a pair of companion connectors, suitably keyway recesses 48 and 50, and also at least one ratchet reverse turn stop 52 and 54 (52 and 54 on collar 36, 52' and 54' on collar 36'). Stops 52 and 54 (and 52' and 54') suitably are an inclined plane with the vertical wall forming the reverse turn stop, and may be situated at any radially equal location on the circumference of collars 36 and 36' respectively which does not interfere with attachment of funnel 60, described below. (In FIG. 4, stops 52 and 54 are for convenience illustrated at 90 degrees rotation from their location depicted in FIGS. 1, 3, 6 and other like side sectional schematic views.)

Figure 5:
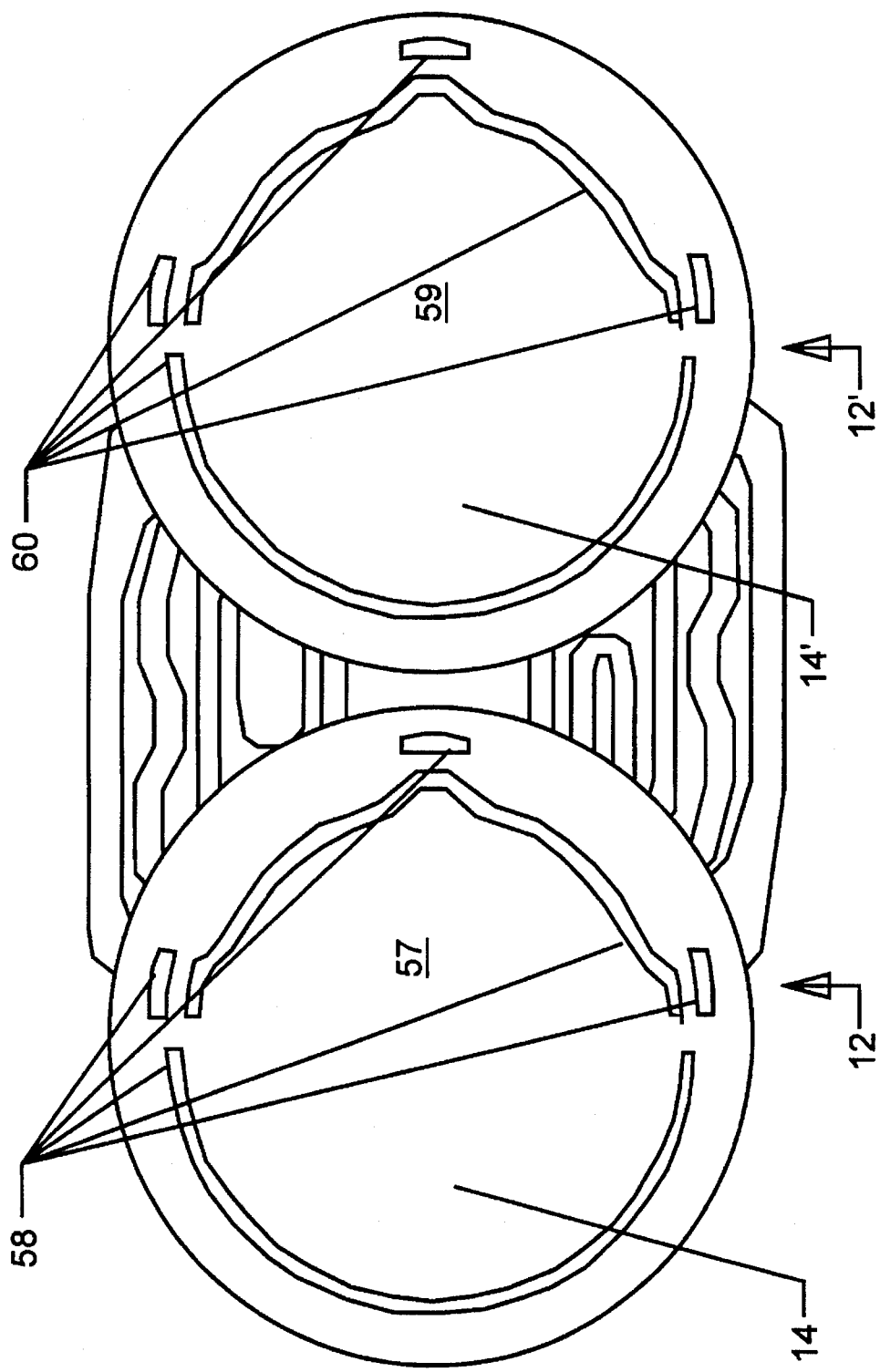
FIG. 5 is a schematic bottom plan view of two containers of a vessel assembly of this invention.

Referring to FIG. 5, a bottom view of containers 12 and 12' shows the underside of container floor 14. Floor 14 of one container (12) has on the underside 57 thereof one member 58 of a coupling interlock, and floor 14' of the other container (12') has on the underside 59 thereof the other member 60 of the coupling interlock. Other suitable coupling devices may be used.

Figure 6:
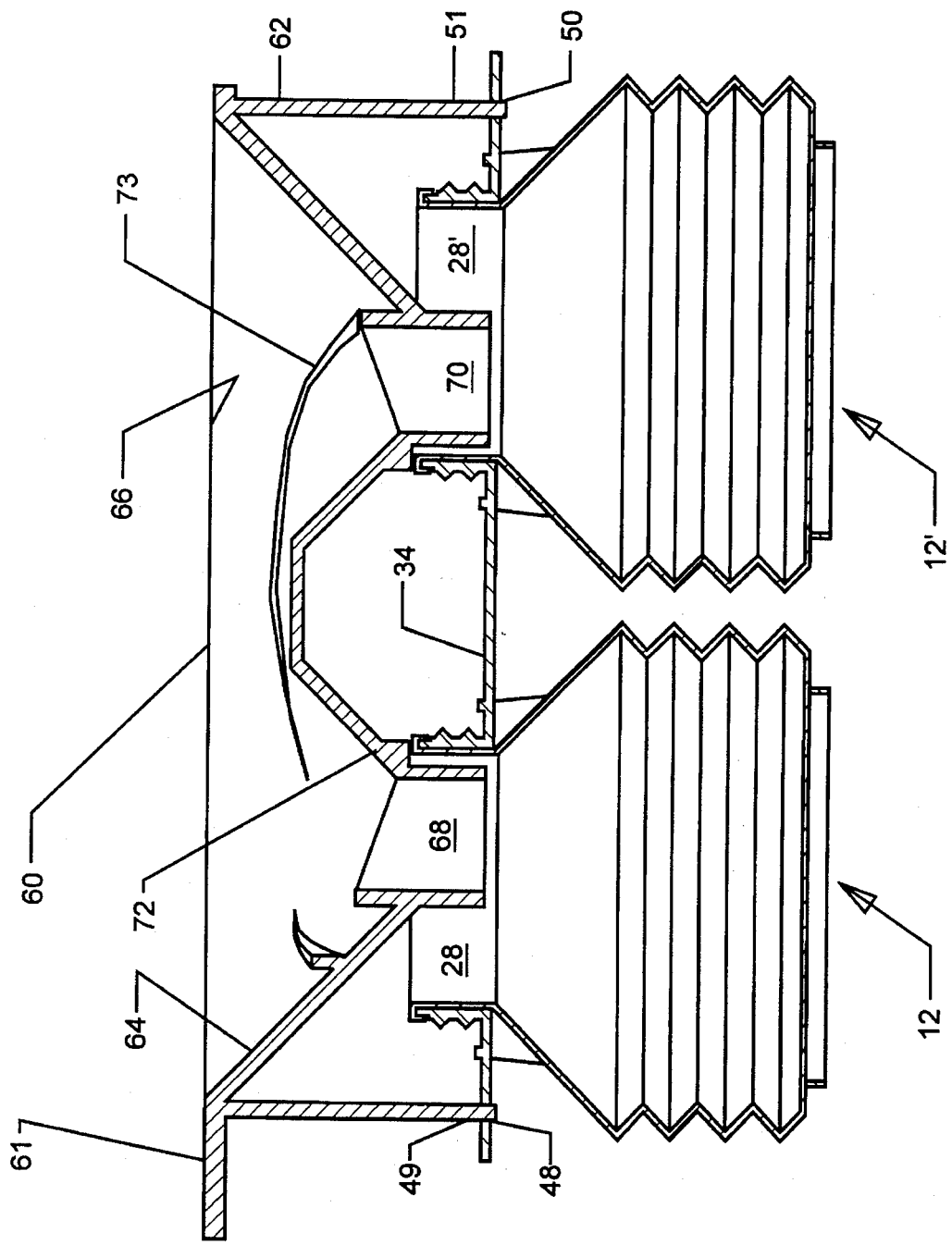
FIG. 6 is a schematic side vertical sectional view of an assembly of two containers joined by a retainer connecting a funnel of a vessel assembly of this invention.

Referring to FIG. 6, split sample vessel assembly 10 includes containers 12 and 12' fixedly connected by retainer 34 and includes a funnel 60 releasably attached to companion members 48 and 50 of retainer collar portions 36 and 36'. Funnel 60 has the other member 49 and 51 of collar companion means 48 and 50. Funnel companion members 49 and 51 suitably are terminals depending on fingers extending from the bottom of an upper external portion of funnel wall 64. Funnel companion members 49 and 51 key into the complimentary portion of the keyway recesses 48 and 50. With terminals 49 and 51 inserted into the complimentary portion of the keyway recesses 48 and 50, the funnel is rotated slightly to move terminals 49 and 51 under slot portions of the keyways which accept the fingers of companion members 49 and 51.

Figure 7:
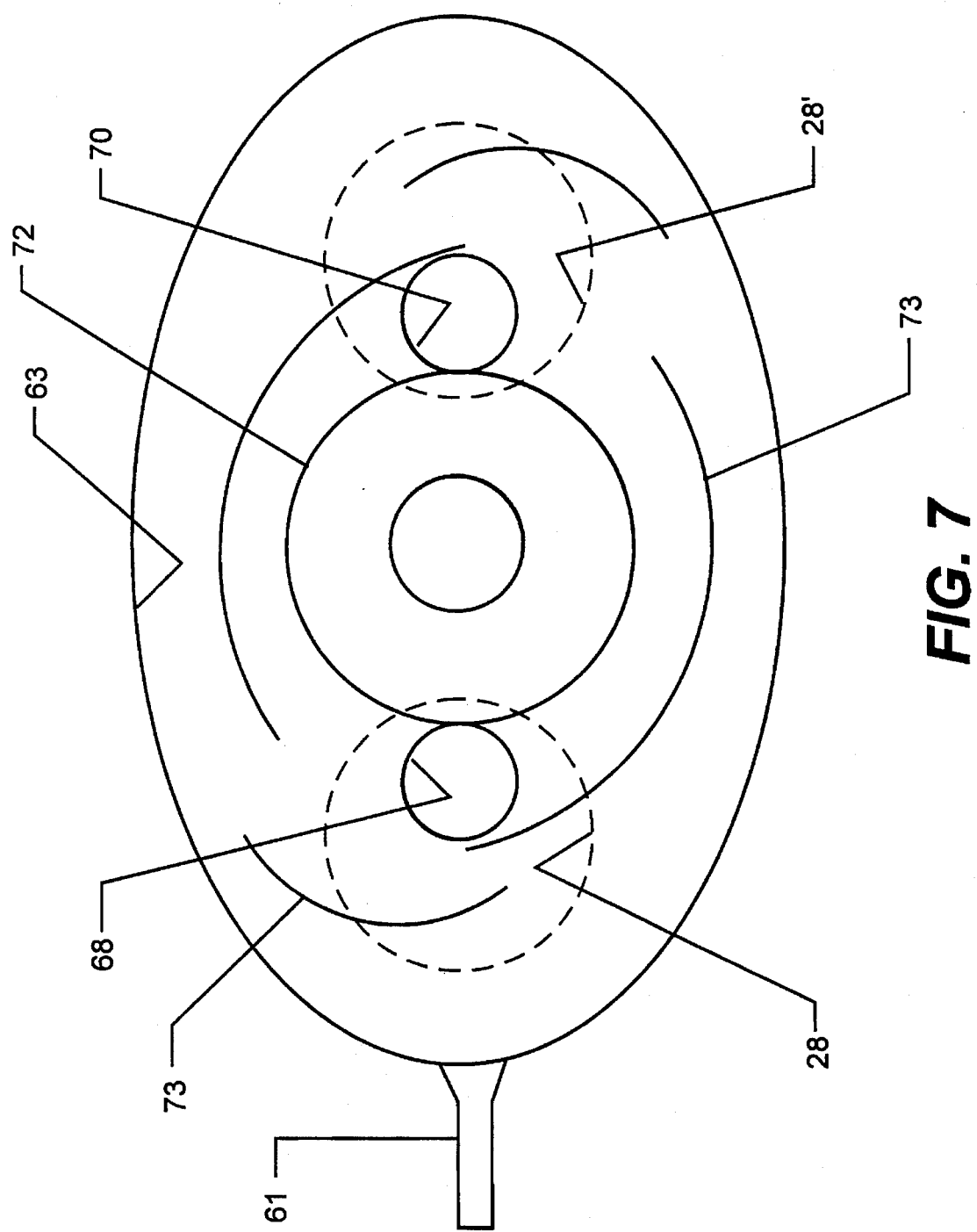
FIG. 7 is a schematic top plan view of a funnel of a vessel assembly of this invention.

Referring to FIGS. 6 and 7, funnel 60 comprises the funnel wall 64 tapering inwardly from an upper entrance opening 66 to two lower spout outlets 68 and 70 spaced apart to empty into the spaced throats 28 and 28' of containers 12 and 12'. Between funnel entrance opening 66 and spout outlets 68 and 70, a distributor 63 comprises a diverter 72 and baffles 73 for distributing flow of a liquid admitted through funnel entrance opening 66 to both spout outlets 68 and 70. A series of baffles 73 which suitably overlap one of their number on one end thereof distribute entering liquid flow to both spouts 68 and 70. Diverter 72 separates flow between spouts 68 and 70. A handle 61 is formed at one end of the container. The handle suitably extends in substantially the direction of a line connecting the axes of the funnel outlets. A principal intended use of the vessel assembly 10 is for urine collection and urine specimen aliquoting, and it will be appreciated that the handle makes the vessel assembly gender friendly for females. Handle 61 is illustrated schematically in a horizontal disposition, but may be angled upwardly for donor convenience.

Figure 8:
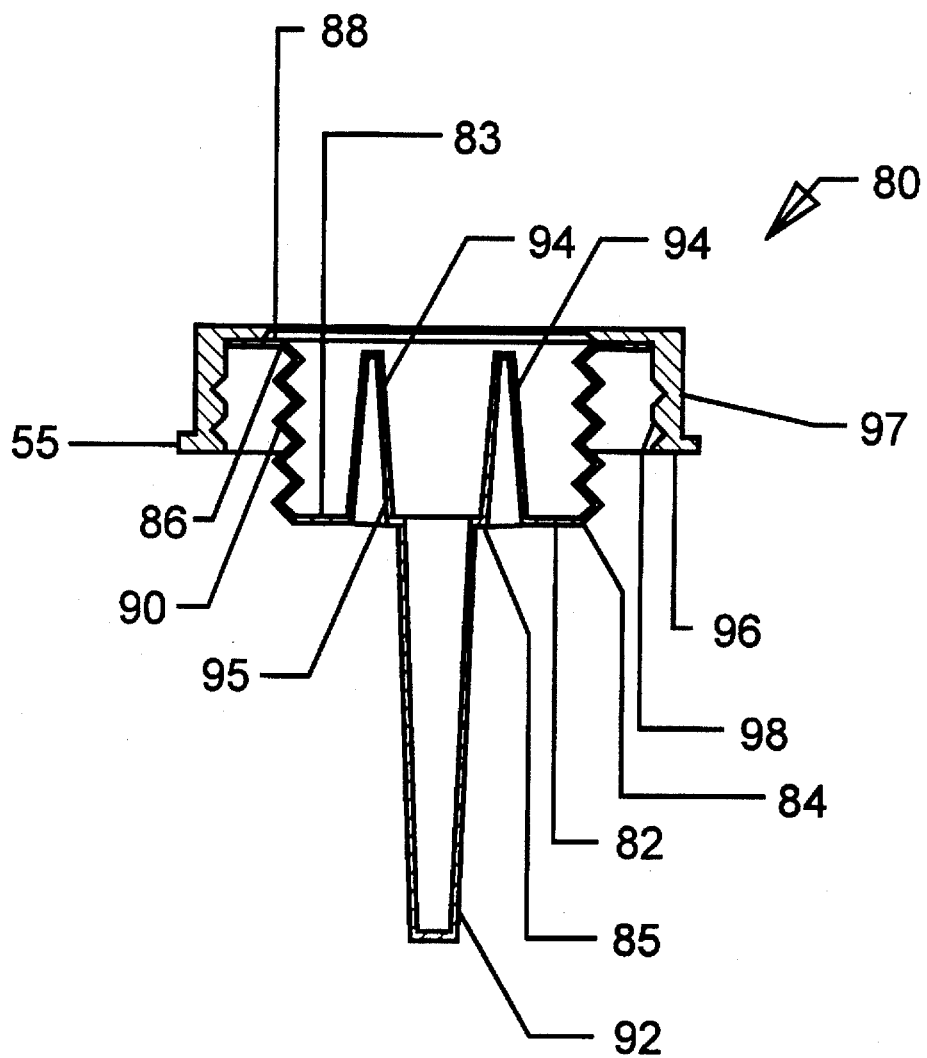
FIG. 8 is a schematic side vertical sectional view of a closure cap for a container of a vessel of this invention.

Referring to FIG. 8, a closure 80 for container 12 includes a stiff base 82 smaller than the opening 28 in container 12. A sidewall 84 of closure 80 is connected at a lower portion of the sidewall to the base 82. Sidewall 84 has an upper portion 86 comprising a flange 88 extending radially outwardly to rest on the rim 24 of container 12. Closure sidewall 84 further includes a flexure portion 90 below flange 88. Sidewall flexure portion 90 suitably is a bellows or accordion-like structure in which concentric rings or pleats are molded as an expansion element. The expansion element may also take the form of a spiral.

Closure base 82 has a topside 83 and a bottomside 85. Bottomside 85 includes a dependent stiff suitably hollow projection 92 of length to extend adjacent the upperside 15 of container floor 14 upon closure of the container. Topside 83 includes at least one upstanding nozzle 94 opening at 95 only to bottomside 85.

Closure 80 also comprises a cap portion 96 with a dependent flange or downflange 97 having internal threads 98 cooperative with the external threads 40 on said retainer (FIG. 1) or container neck 22 (FIG. 1). Closure 80 includes a ratchet member 55 slideable in the forward turn direction only over ratchet reverse turn stop 52 or 54. The forward turn direction is the direction in which closure 80 is turned to screw the closure 80 by the threads 98 onto the container 12. Ratchet reverse turn stop 52 or 54 is configured to prevent a movement of the cap in the reverse direction, thereby locking closure 80 onto container 12 when closure 80 is screwed on. Thus, after a urine specimen is placed in container 12 and closure 80 is screwed on, the urine specimen is sealed and locked in vessel 10.

Container sidewall flexure portion 32 (FIG. 1) provides an intra-container pressure control regulation, assisted by closure flexure portion 90 (FIG. 8). When containers 12 and 12' are sealed with closure 80 after containers 12 and 12' are partially or fully filled with liquid, the interior of the containers is at the ambient pressure of the place of filling. The containers 12 and 12' at least below the neck 22 are relatively rigid. In the absence of flexure portions 32, transfer from the place of filling to a place of higher or lower ambient pressure could cause significant pressure changes that would not be compensated by the material of the container, or by any appreciable compression by air which may be found in the primary specimen vessel. This pressure differential possibly could disrupt the container sealing and cause leakage. With flexure sidewall portions 32 and 90, any pressure differential between ambient and the interior of the primary specimen vessel will equilibrate by distention or contraction of the bellows rings or pleats.

In accordance with this invention, the fundamental or initial steps of the invention for handling a liquid specimen comprise (1) placing a liquid specimen in container 12, and (2) closing container 12 with closure 80. The method of handling a liquid specimen in this invention includes not only the use of the single vessel 10 but also use of a vessel assembly in which container 12, as has been described above, is fixed by retainer 34 side by side with another like container 12'. In this connection, the method optionally further comprises in step (1) placing a specimen in each of the containers 12 and 12', and in step (2) closing each of the containers 12 and 12'. This method includes applicability of funnel 60, and in step (1) includes placing the liquid specimen into entrance opening 66 of funnel 60 releasably connected to containers 12 and 12', funnel 60 including wall 64 tapering inwardly from upper entrance opening 66 to two lower outlets 68 and 70 positioned below funnel opening 66, funnel 60 between entrance opening 66 and outlets 68 and 70 having distributor 63 for distributing specimen to both said outlets 66 and 68. The method further comprises, after step (1) and before step (2), disconnecting said funnel from said vessel.

Figure 9:
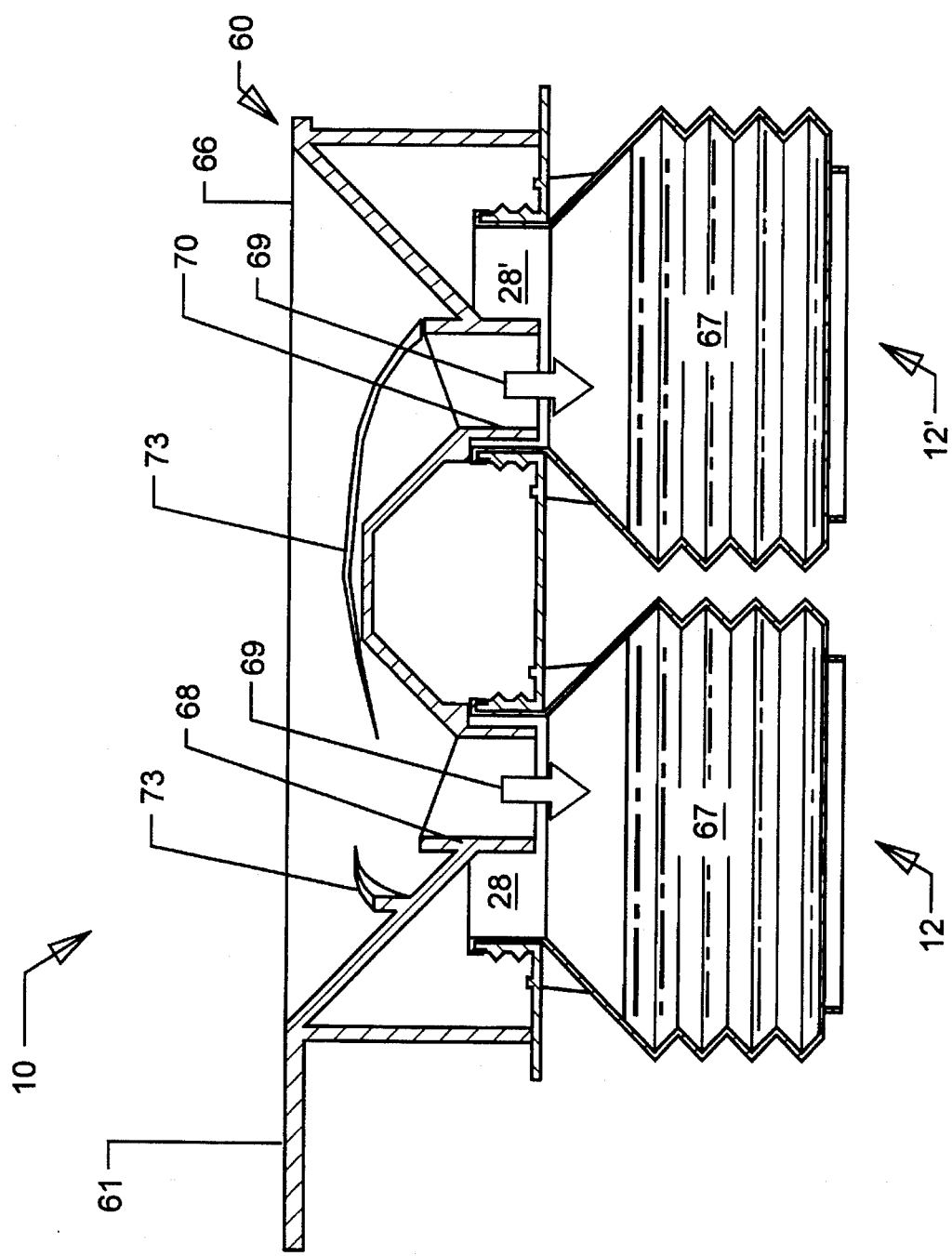
FIG. 9 is a schematic side vertical sectional view of the assembly of FIG. 6 with arrows indicating an addition of a liquid specimen to the vessel assembly.
Figure 10:
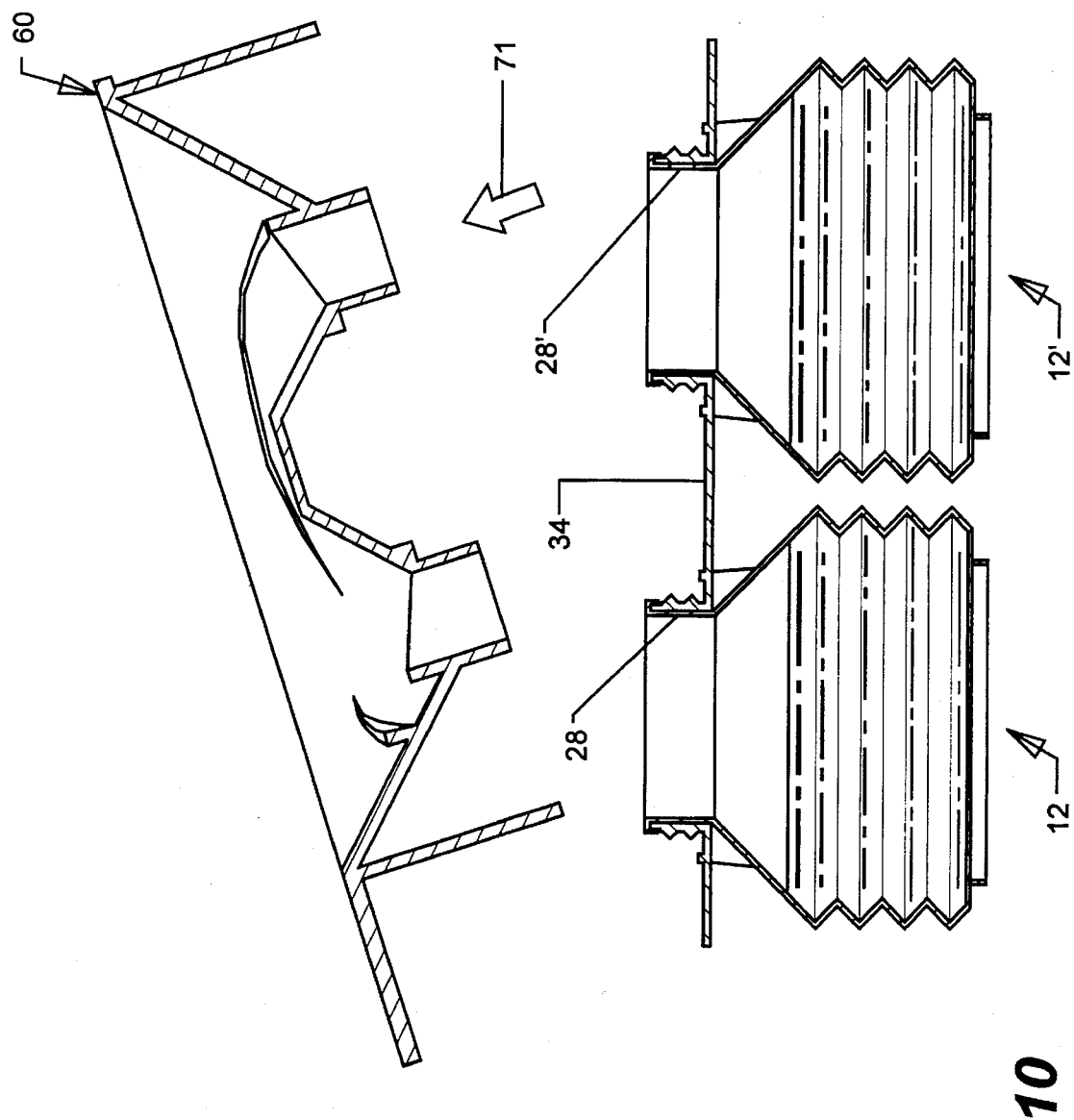
FIG. 10 is a schematic side vertical sectional view of the assembly of FIG. 9 showing a separation of the funnel portion of the vessel assembly.
Figure 11:
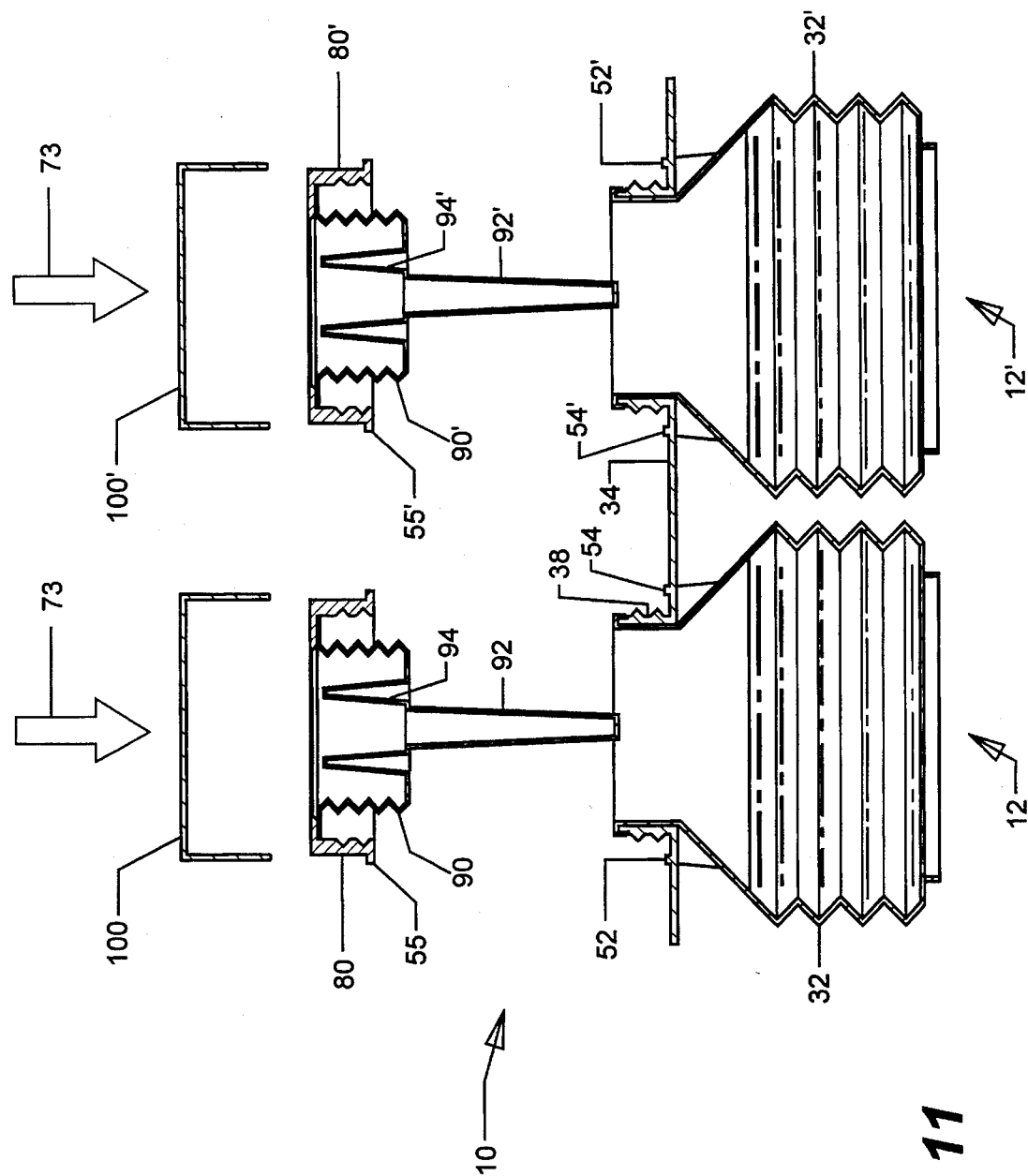
FIG. 11 is a schematic side vertical sectional view showing the caps of the vessels of this invention positioned for closure of the containers of the assembly of FIG. 10.

Accordingly, at a place of specimen collection a vessel assembly 10 in the assembly state shown in FIG. 6 is removed from a sealed wrapper. In a typical chain-of-custody procedure, the donor, typically after completing a multicopy requisition, is given the vessel assembly depicted in FIG. 6. The collector retains the vessel closures 80. Referring to FIG. 9, the specimen donor privately urinates into the funnel 60 through upper entrance opening 66. Urine (indicated by numeral 67) is distributed by baffles 73, and diverted by diverter 72, flows from funnel 60 through funnel spouts 68 and 70 and container openings 28 and 28' into containers 12 and 12', as indicated by arrows 69. The donor returns the vessel assembly inclusive of funnel 60 to the collector, who, as indicated in FIG. 10, unlocks the funnel from the vessel assembly inclusive of the containers 12 and 12' and retainer 34. This is done by rotating the funnel slightly to align the terminal extensions of funnels companion members 49 and 51 with the complimentary portion of the keyway recesses 48 and 50 and then lifting the funnel from the retainer recesses 48 and 50, as indicated by arrow 71. The collector discards the funnel. Referring to FIG. 11, the collector then closes the containers 12 and 12', as indicated by arrows 73, using closures 80 and 80', by screwing the closures onto collar barrel 38 in the embodiment illustrated. The action of the cap ratchet 55 and ratchet stops 52 and 54 locks the cap to the container collar 36. The collector then suitably may place a tamper evident tape 100 across each closure cap 80 and onto the sides of containers 12 (tapes 100 and 100' on caps 80 and 80' of containers 12 and 12' in FIG. 11). The donor typically initials tapes 100 and 100'. Split sample vessel assembly 10 comprising the containers 12 and 12' connected by retainer 34 and closed by closures 80 and 80' is now ready for delivery to a testing laboratory.

For delivery, typically a split sample vessel assembly 10 is placed in one compartment of a two compartment mailing pouch. The requisition is typically signed by the donor and collector, a copy of it is given to the donor and a file copy is retained by the collector. The remainder of the requisition typically is placed in the second compartment of the pouch. The pouch is then sealed and delivered to a testing laboratory, where a specimen or aliquot of the specimen in the vessel assembly will be removed for analytical testing. Bellows 32 and 32' permit containers 12 and 12' to expand or contract upon exposure of the vessel assembly to any materially lower or higher ambient pressure either during transit or at the destination. Bellows 32 and 32' therefore assure that the ambient pressure changes to which split sample vessel assembly 10 is exposed do not cause the vessels to leak.

Figure 12:
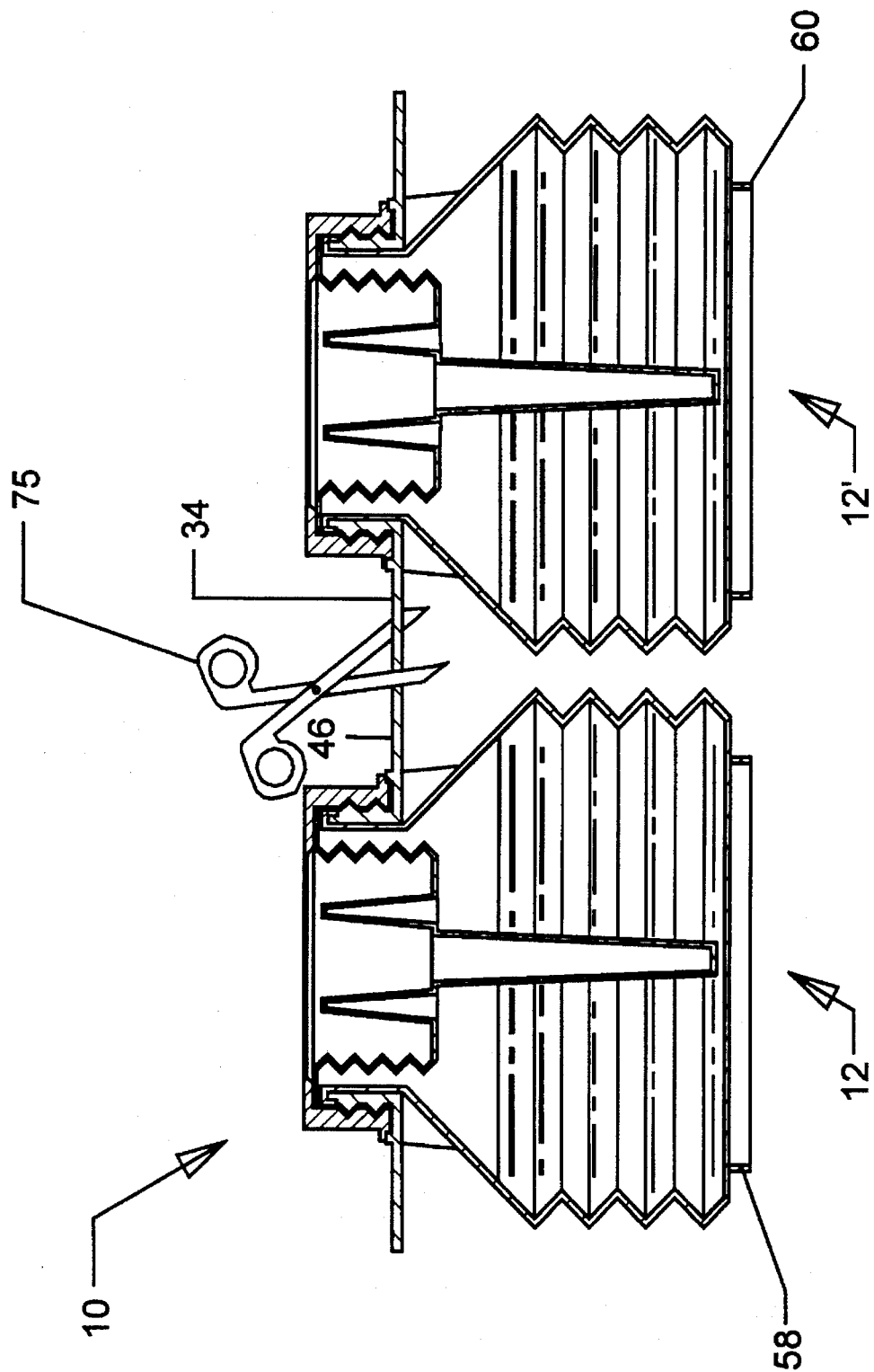
FIG. 12 is a schematic side vertical sectional view of the vessels of this invention closed with caps after removal of the funnel, with scissors indicating severance of a fixing portion of the retainer illustrated in FIG. 4.
Figure 13:
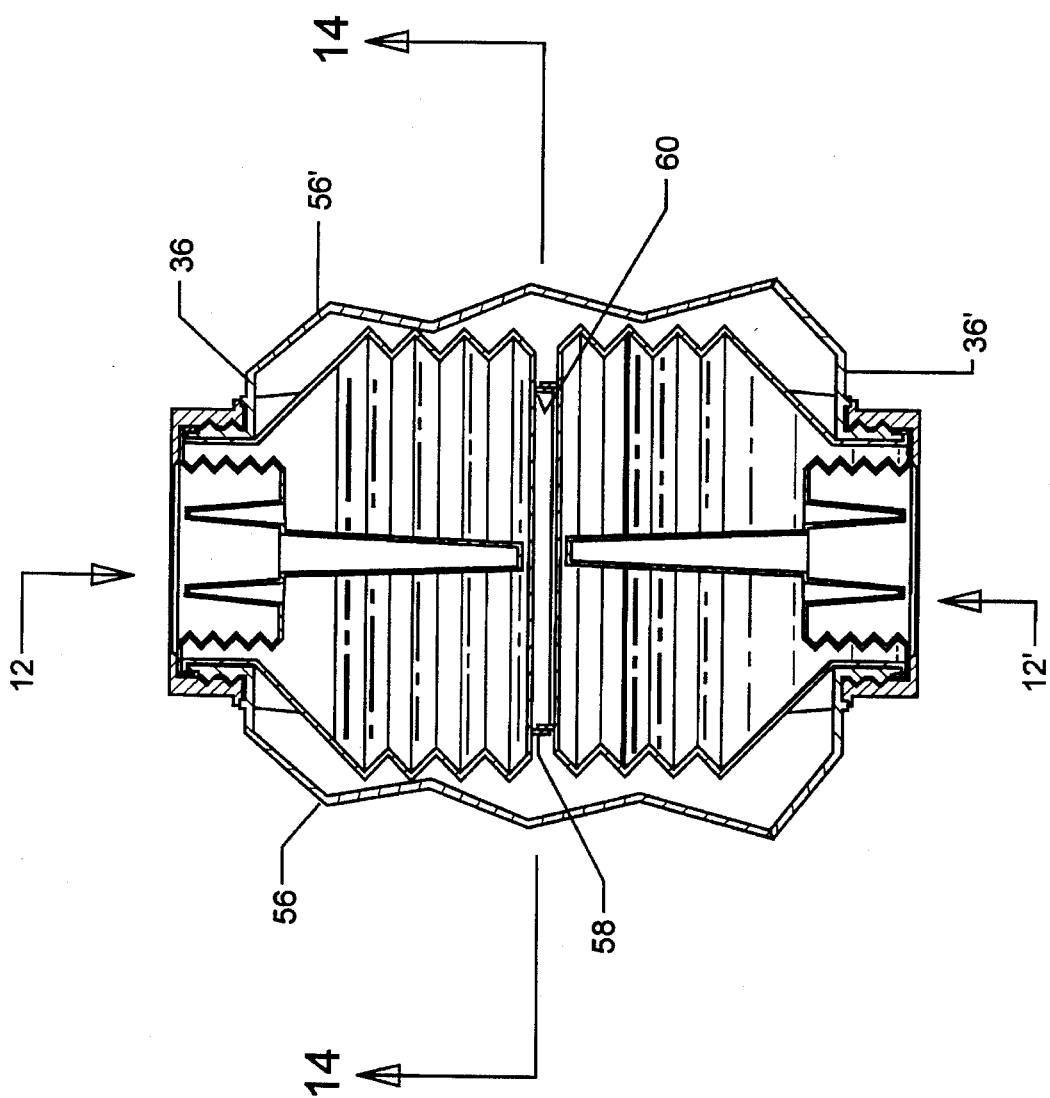
FIG. 13 is a schematic side vertical sectional view of the vessels of this invention interconnected at the floor of the containers and linked by a serpentine portion of the retainer illustrated in FIG. 4.
Figure 15:
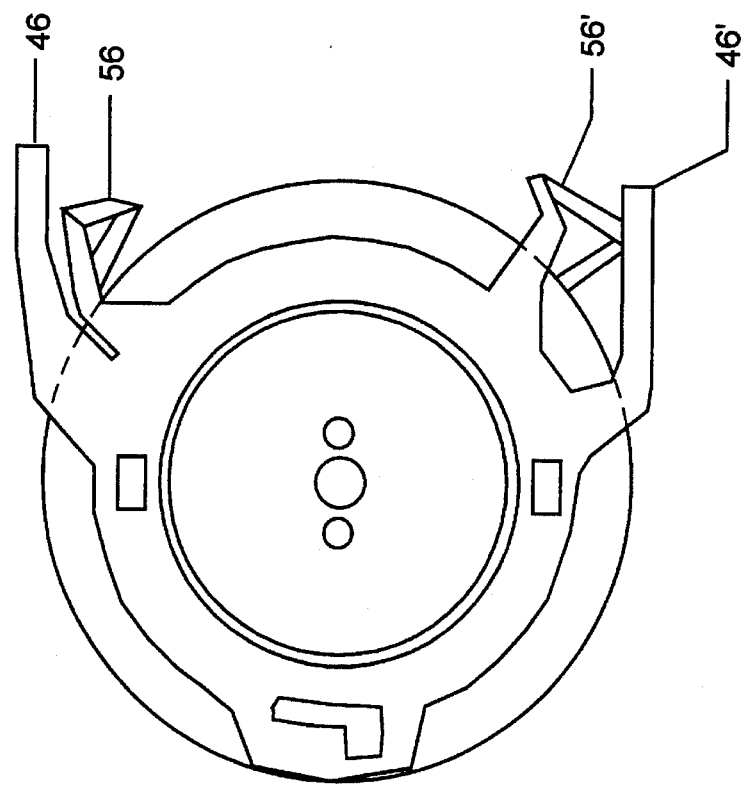
FIG. 15 is a schematic top plan view of the severed retainer of FIG. 5 attached to the top containers in FIG. 13.
Figure 14:
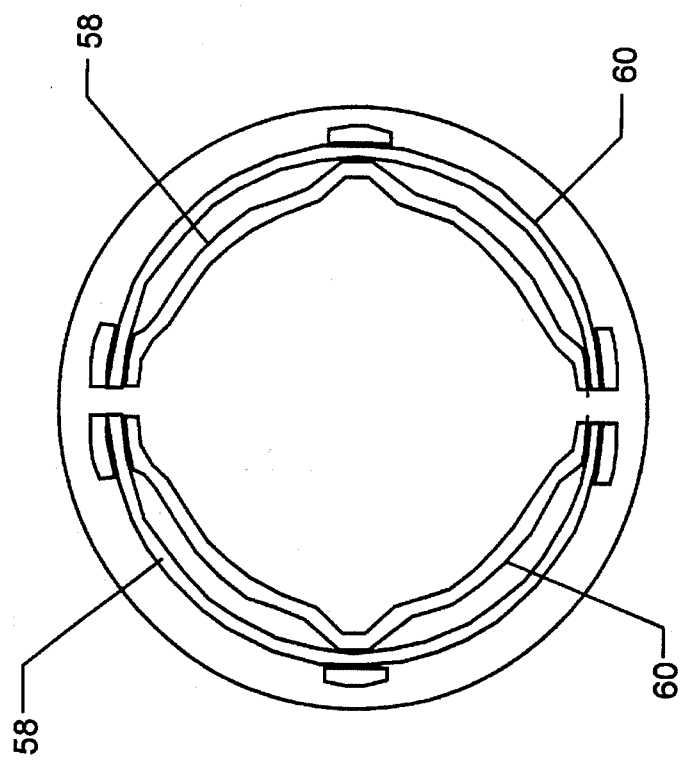
FIG. 14 is a schematic bottom plan view taken along the line 14—14 of FIG. 13 illustrating the coupling of the container interlock shown in FIG. 5.
Figure 16:
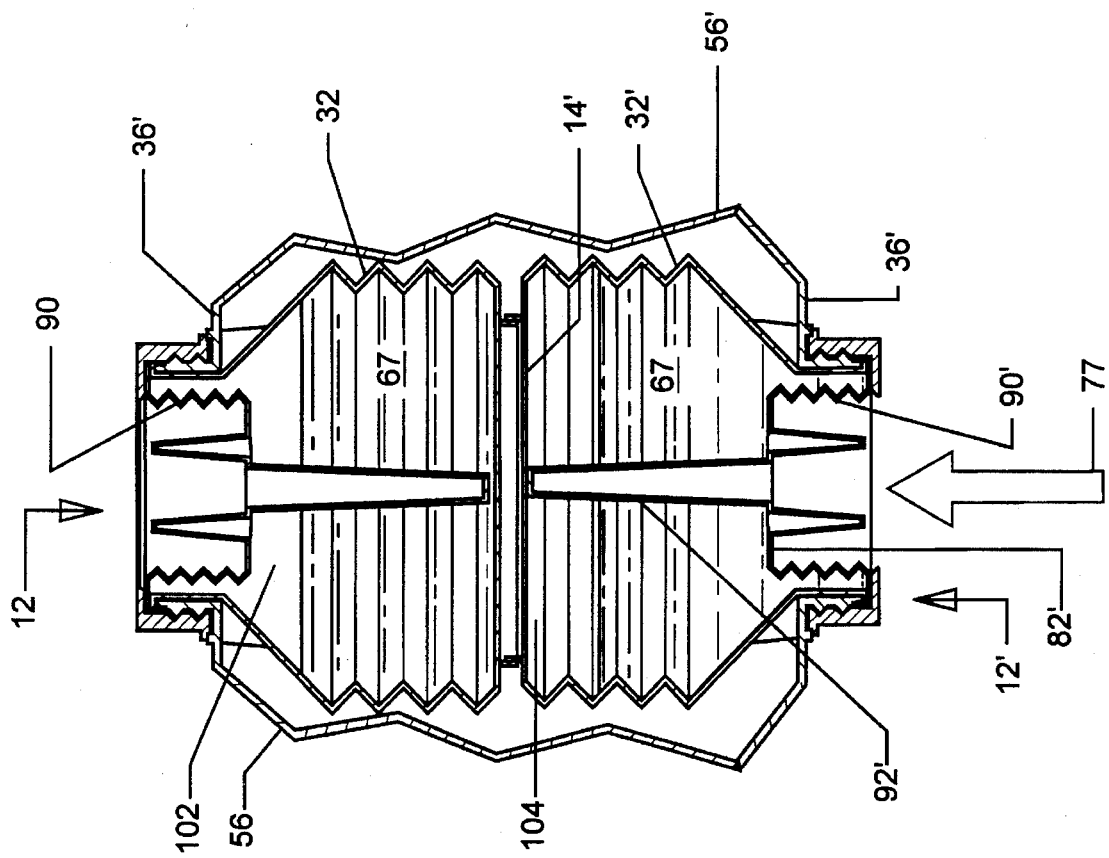
FIG. 16 is a schematic side vertical sectional view of the vessels of FIG. 13 with an arrow indicating a direction of force applied to the base of the closure of the bottom container.

At the destination, the testing laboratory continues assurance of chain-of-custody of the vessel assembly. Typically a technician removes the vessel assembly and the requisition from the pouch and attaches identical bar code labels from a set, one to the requisition, one to container 12 and another to container 12'. The same label on containers 12 and 12' assures that identification of the specimen in container 12 is the same as in container 12'. As indicated by the scissors 75 in FIG. 12, the rigid distance fixing portions 46 and 46' are severed by a technician. Suitable severance locations are indicated at 47 and 49 of FIG. 4. Referring to FIGS. 13, 14 and 15, one of the containers 12 and 12' is then inverted, say 12', and members 58 and 60 of the coupling interlock pair on the floor undersides of containers 12 and 12' are coupled, as seen in FIG. 13. Coupled, they appear as in FIG. 14. Serpentine connectors or ties 56 and 56' interconnect the collar portions of retainer 34. The severed fixing portions 46 and 46' are seen in FIG. 15, as are the serpentine connectors 56 and 56'. While two serpentine connectors are shown, one is suitable. Referring to FIG. 16, it will be seen that any air captured in the container when it is closed is above the top surface of the urine in upright container 12 (and in the example illustrated, below base 82 of closure 80 of container 12) as indicated by reference numeral 102. In inverted container 12', any captured air is interposed between the top surface of the urine and floor 14' of container 12', as indicated by reference numeral 104.

Alternative to the foregoing division of vessel assembly manipulation between the collector and the destination technician, the collector may sever the fixing portions 46 and 46', invert one of the containers 12 and 12' and couple them, leaving them attached by serpentine connectors 56 and 56', and then place the coupled and attached containers 12 and 12' in the delivery pouch. In such instance, upon arrival of the coupled and attached containers 12 and 12' at the place of destination, the bar code or other suitable labels are affixed to the containers 12 and 12' as already described.

After the foregoing manipulations of the split sample vessel assembly by either example, the tamper proof tape 100' is then removed from inverted container 12' (and is shown removed in FIG. 16), exposing base 82'. Vessel assembly 10 is now ready for actuation for removal of an aliquot from the split urine specimen in container 12'.

As has been described above, projection 92 from the bottomside 85 of closure base 82 extends adjacent container floor 14. The term "adjacent" is intended to include both an embodiment in which the end of projection 92 approaches near but does not contact the upperside of floor 14, as well as an embodiment in which the end of projection 92 contacts the upperside 15 of floor 14. The former embodiment is preferred and its use and action will be described first. The actions taken on container 12' described below suitably are accomplished by reciprocation of a shaft with a radially expandable end that inserts into hollow projection 92 and then expands to grip projection 92. The shaft is not shown.

In the aspect of this invention in which projection 92 does not contact the upperside 15 of container floor 14, the steps for handling a liquid sample, after having (1) placed the sample in the container and (2) closed the container, further comprise:

(3) inverting closed container 12 not later than just before step (7) described below, that is, suitably before any one of steps (4)–(7) described below, preferably before step (4);

(4) advancing projection 92 of the closure base in the closed container sufficiently toward container floor 14 while maintaining the container stationary, first to extend flexure sidewalls 90 of closure 80 and push projection 92 of the closure base into contact with the upperside 15 of container floor 14, then to extend flexure sidewalls 32 of container 12, thereby enlarging the volume within container 12 and reducing the intra-container pressure;

(5) while maintaining the sidewall extensions imparted in step (4), creating an aperture in nozzle 94 remote from the opening 95 thereof, thereby to equilibrate the intrachamber pressure of container 12 with ambient pressure;

(6) moving projection 92 of the closure base in a direction away from and contact with container floor 14 sufficiently to reduce the extension of flexure sidewalls 90 of the closure and 32 of the container (and thereby decrease the volume within the container and increase the intra-container pressure) without forcing any liquid from the container through the created aperture; and (7) advancing projection 92 of the closure base of the inverted container 12 toward the floor 14 thereof while maintaining the inverted container 12 stationary, to extend the flexure sidewall 90 of the closure 80, without contacting the inverted container floor 14 with the closure projection 92, sufficiently to further decrease the volume of the inverted container and further increase the intra-container pressure to an extent effective to expel liquid from the inverted container through the aperture.

Supplementing the foregoing steps, the method further comprises sealing an opened nozzle 94 of an inverted container 12, and in the case of the case where the containers 12 and 12' are coupled, also includes, after the sealing step, decoupling the members 58 and 60 of the coupling pair to separate the containers. In the case where the retainer 34 comprises at least one serpentine connector 56 loosely connecting containers 12 and 12', the method further comprises, after the sealing step, severing the serpentine connector.

It is apparent from the foregoing, and will be seen from the other aspects of handling a specimen according to this invention described below, that an important part of the invention methodology for removal of an aliquot specimen from a container 12 is initially inducing a negative intra-container pressure relative to the ambient pressure by increasing the volume of container 12. Referring to FIGS. 19–26, the sequence of how this preferably is accomplished is illustrated. In these Figures, use of the prime symbol indicates an inverted container 12' and its components; the inverted container 12' may be (but is not necessarily) connected to another container 12.

Figure 19:
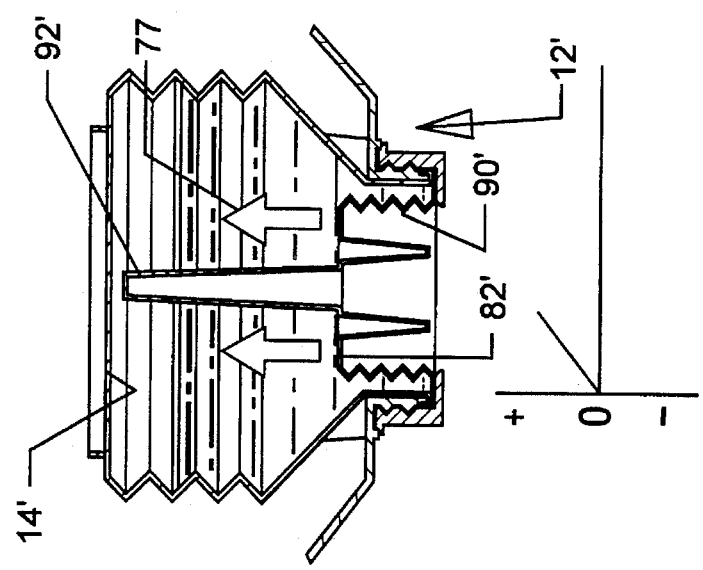
FIGS. 19 through 26 are schematic side vertical sectional views of the one of the vessels of FIG. 18 and under each such view an x-y line graph of intra-container ("cup") historic pressure during the sequential actions on the container illustrated in FIGS. 19 through 26.
Figure 20:
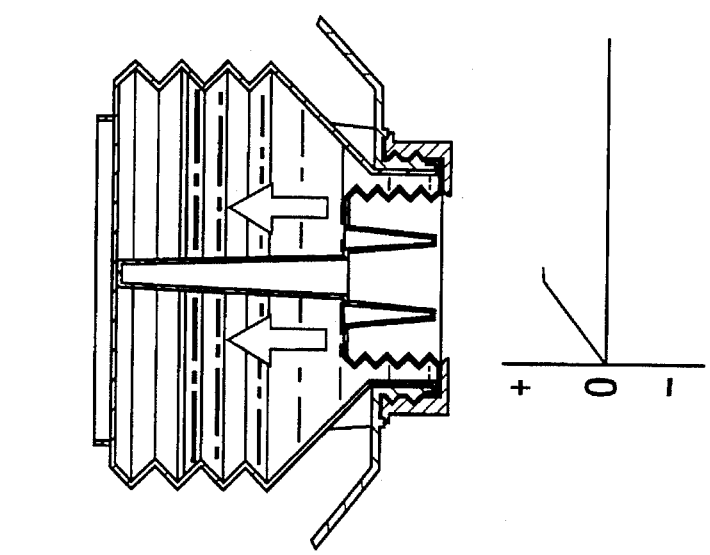
Figure 21:
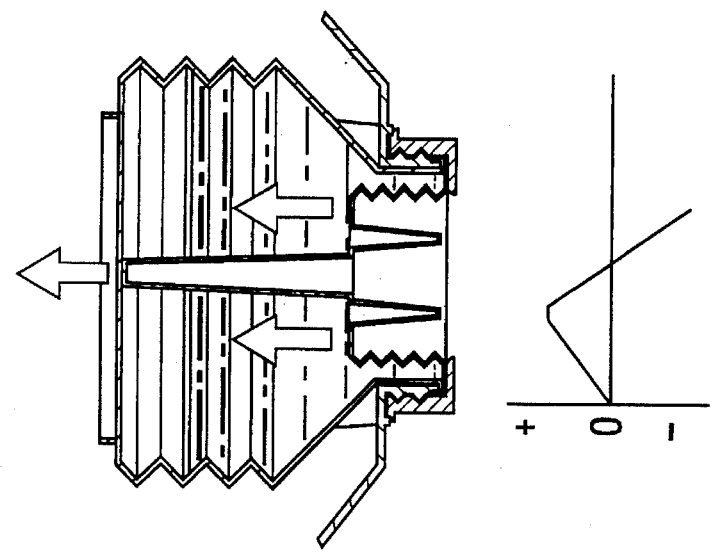

In FIG. 19, as indicated by arrow 77, closure base 82' is pushed toward floor 14' of container 12'. This compresses any air entrapped in container 12' as at 104', reduces the volume in container 12', and increases intra-chamber pressure, as indicated by the line graph of pressure per step below the schematic of the step, in FIG. 19. This also lengthens the flexure or bellows portion 90' of closure 80', allowing projection 92' to move into contact with floor 14', as in FIG. 20. After projection 92' contacts floor 14', further upward movement of projection 92', as depicted in FIG. 21, extends both closure bellows 90' and container bellows 32'. This increases the volume of container 12', and because container 12' is sealed, a negative (or if already negative, a more negative) intra-container pressure is induced relative to the ambient pressure, as depicted by the line graph of FIG. 21.

As illustrated in FIG. 16 for the coupled split specimen vessel assembly, movement of floor 14' of container 12' at the same time also pushes coupled floor 14 of container 12 toward base 82 of container 12. If upward movement of container 12 is restrained, this shortens initially bellows portion 32 of container 12, and any air entrapped in container 12 at 102 is compressed. If floor 14 of container 12 is moved up into contact with projection 92 of container 12, bellows 90 of closure 80 can be compressed. If floor 14 of container 12 is moved further upward, bellows 90 is compressed.

Figures 22, 23, 24:
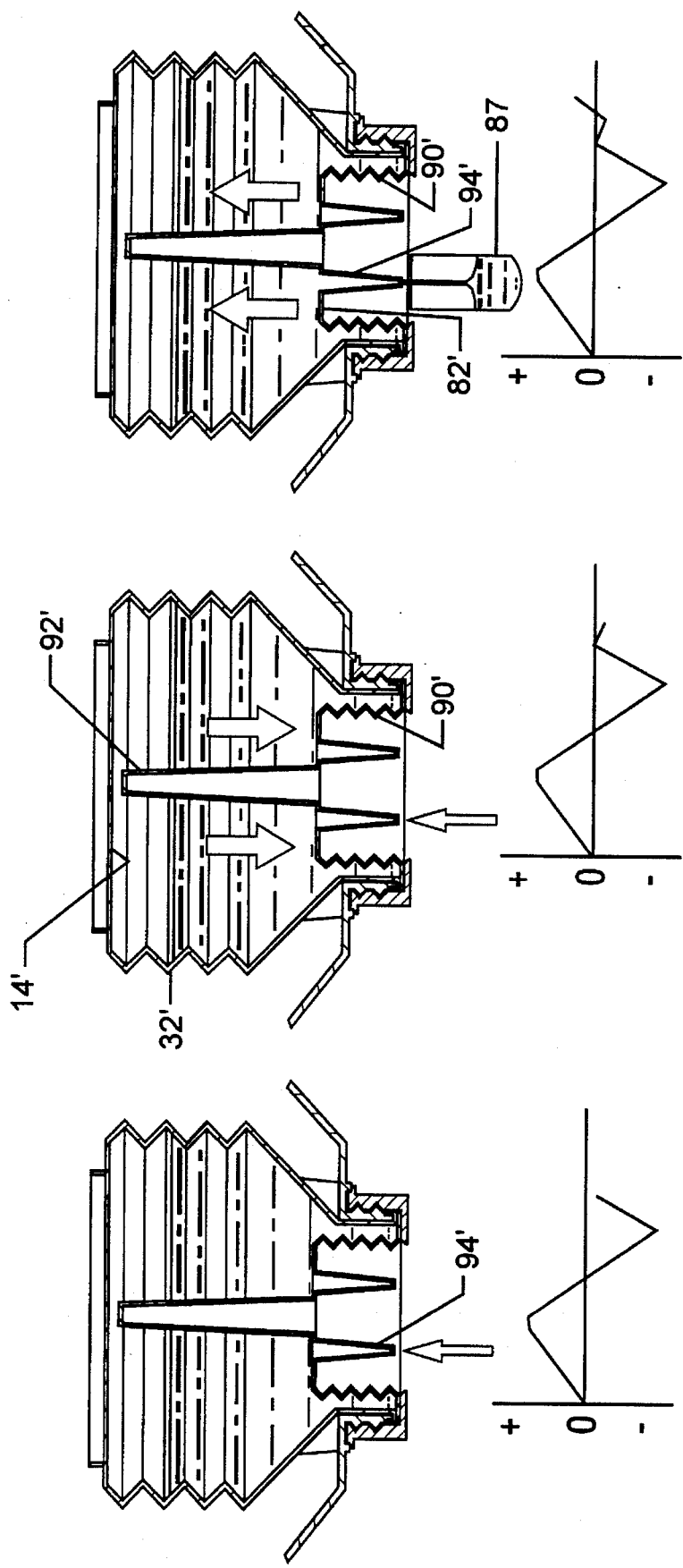
Figures 25, 26:
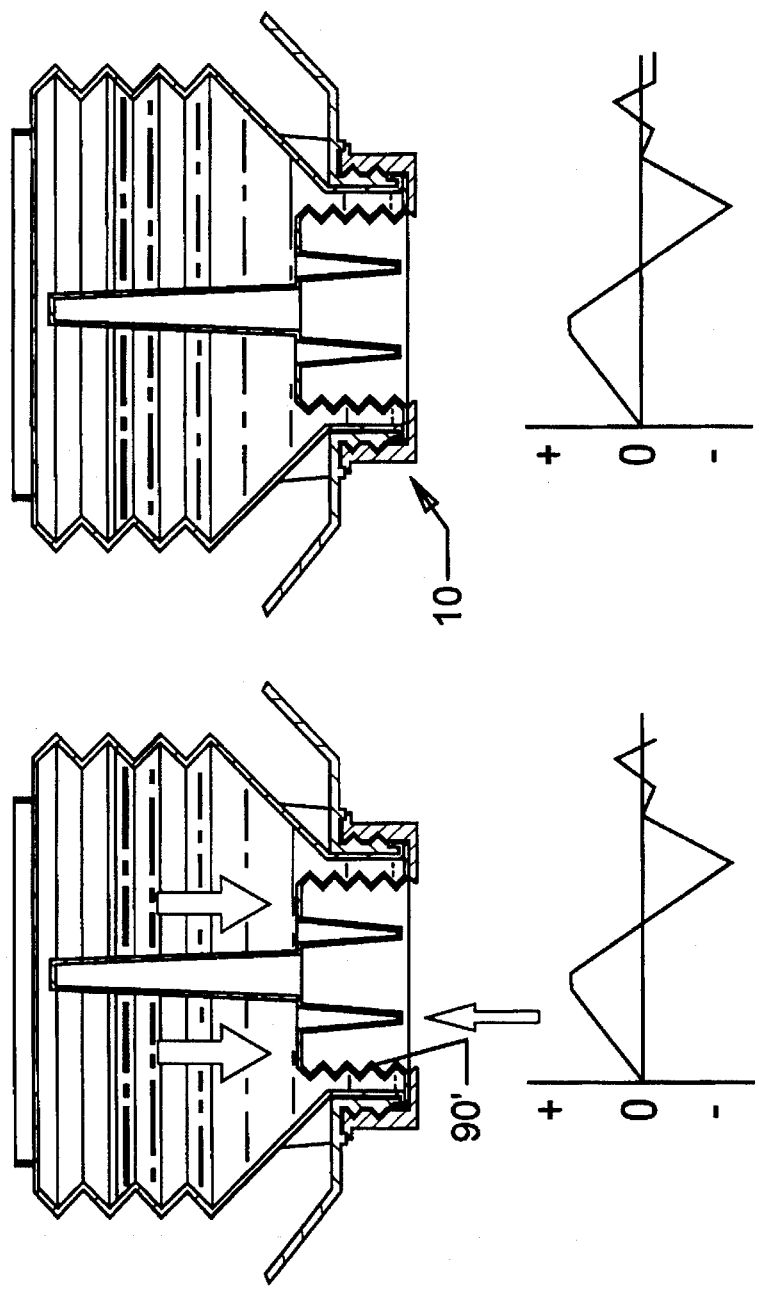

The stiffness of base 82' is sufficient to assure that when base 82' is moved upward, nozzles 94' are maintained in a substantially vertical orientation for ease of opening. With the negative pressure induced in container 12' maintained, as indicated in FIG. 22, a nozzle 94' is opened, preferably non-invasively to assure that anything which can carry a contaminant is not brought into contact with the specimen during the closure opening procedure. By non-invasively creating a hole in the nozzle closure, the integrity of the specimen in container 12' is preserved. A laser system or suitably also a pencil column of heated air may be used to open nozzle 94' non-invasively.

For example, in using a laser system, suitably a laser lens is centered in a laser beam axis to focus the focal point of the lens on the closed end of nozzle 94' placed in coaxial alignment with the laser beam axis. A laser beam shutter is then moved out of the laser beam path and the laser is powered. With the shutter open, the laser emits a beam which is focused by the laser lens onto the closed end of nozzle 94'. The laser energy heats the nozzle closure and melts an opening in the closure.

The opening of nozzle 94' breaches the means of maintaining the pressure differential created by the increased volume created in container 12'. Ambient air at higher pressure rushes upwardly into the nozzle opening and duct into container 12' to equilibrate pressure, as illustrated by the line graph of FIG. 22. This influx of gas and any bubbles formed in the duct by the entering air prevents immediate release of liquid from opened nozzle 94'. Preferably the ratio of the pierced opening diameter to the length of the nozzle duct is maintained sufficiently small also to contribute to resistance of liquid flow from the opened nozzle. After a sufficient exposure time to melt an opening, a laser shutter is moved across the beam and the laser is powered down.

Next, as depicted in FIG. 23, base 82' is pulled down slightly, shortening closure bellows 90' of container 12' and disengaging projection 92' of container 12' from floor 14' of container 12'. As projection 92' of container 12' withdraws, bellows 32' of container 12' shortens and resumes its native position. The opening created in nozzle 94' is such that the aspect of the opening to the length of the nozzle, optionally aided by air bubbles drawn into the nozzle when the nozzle is opened, provides a surface tension sufficient to retain liquid in the container during the disengagement of projection 92' from floor 14' of base 12'.

Figure 17:
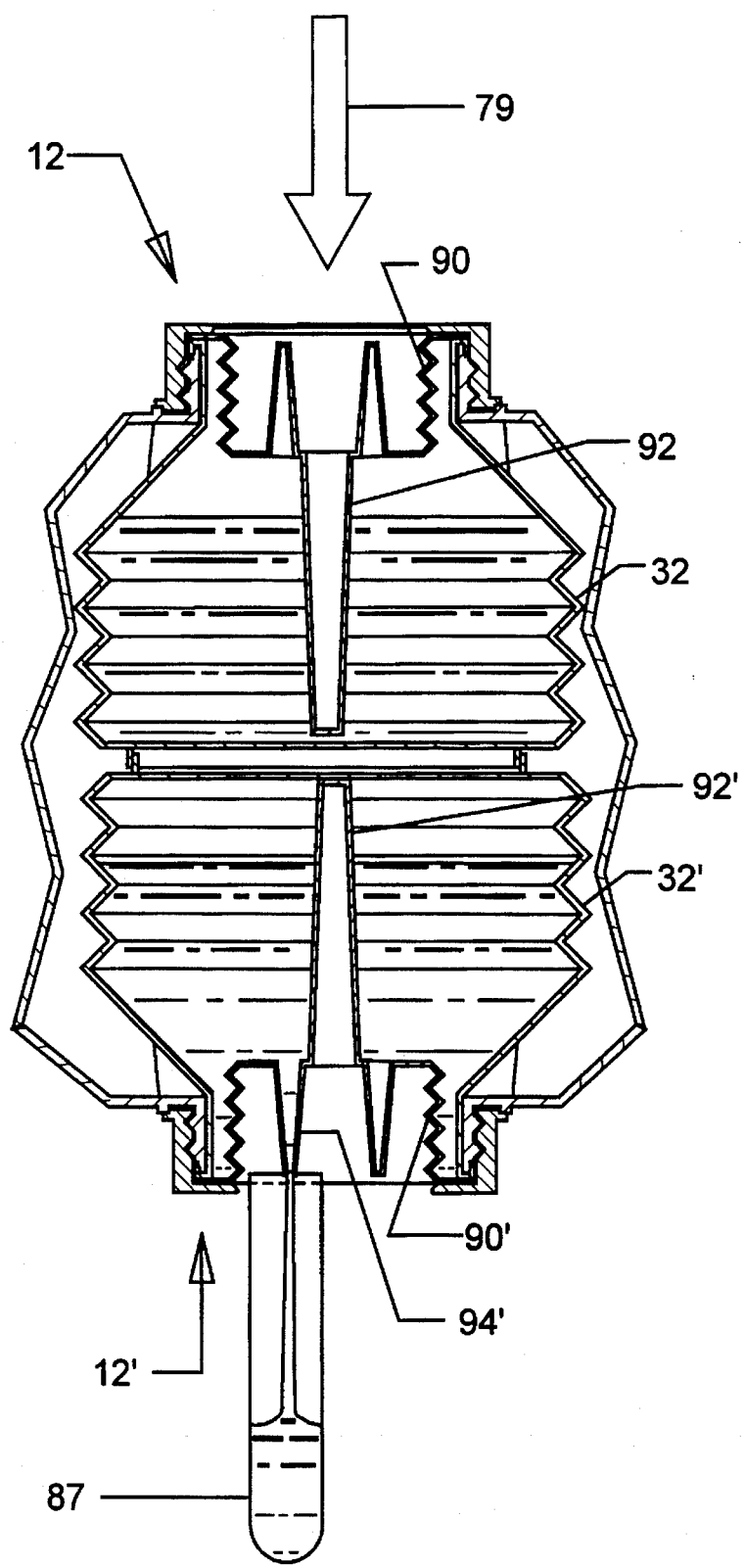
FIG. 17 is a schematic side vertical sectional view of the vessels of FIG. 16 with an arrow indicating a direction of force applied to the closure of the top container and showing filling of an aliquot tube with a liquid specimen from an accessed container.
Figure 18:
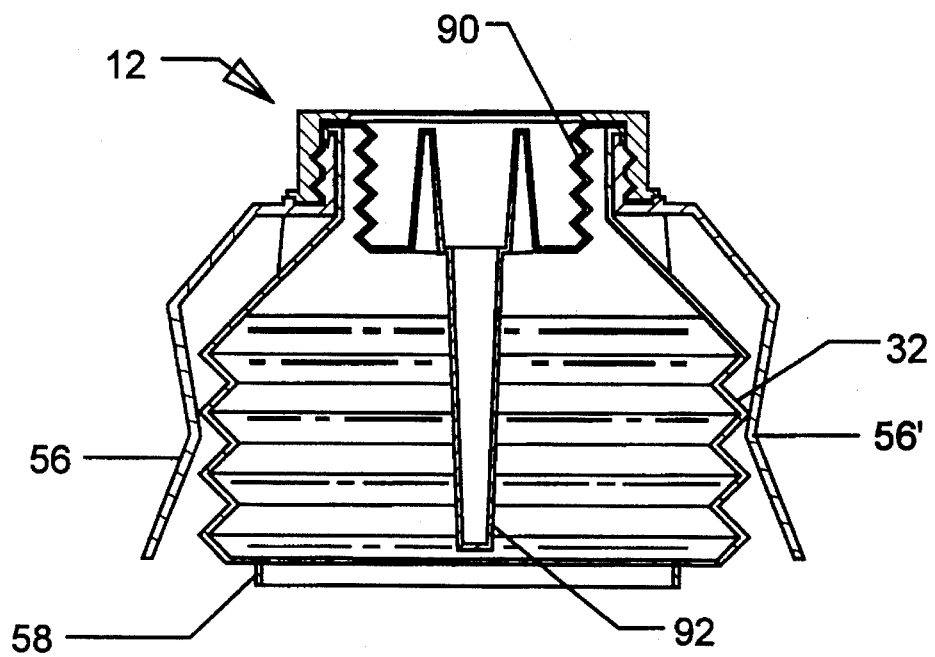
FIG. 18 is a schematic side vertical sectional view of the vessels of FIGS. 13–17 with scissors indicating severance of the serpentine portions of the retainer illustrated in FIG. 4 for separation of split liquid specimens.
Figure 18:
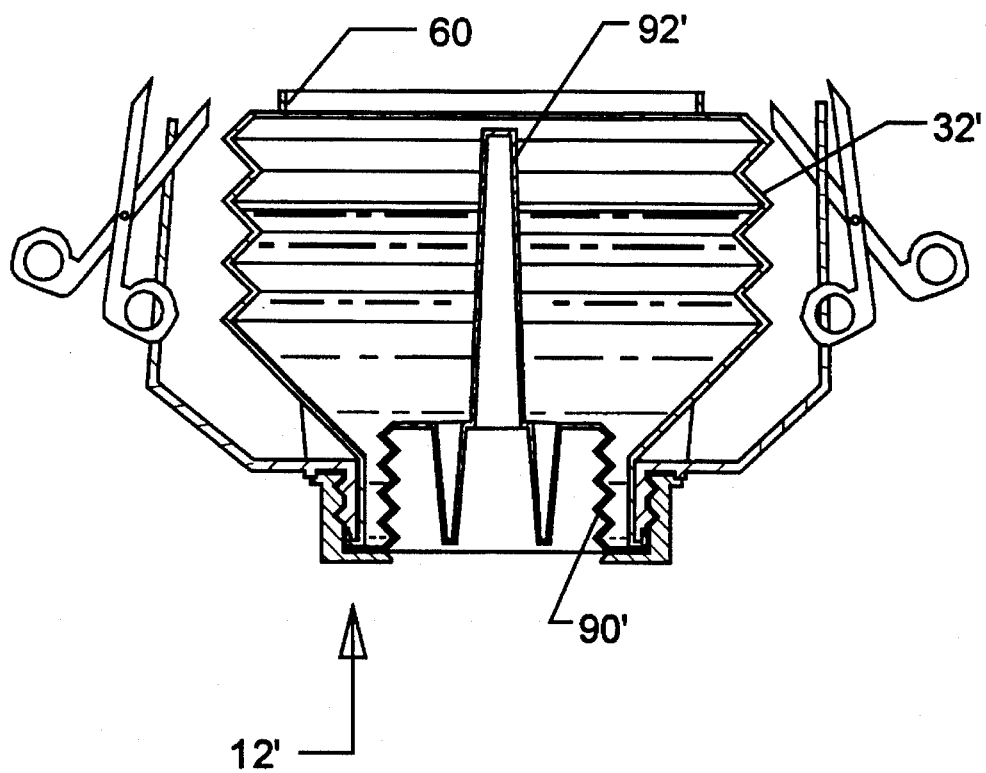

Next an aliquot tube 87 is placed under the opened nozzle 94', either by moving the aliquot tube 87 under the nozzle or by rotating the vessel assembly 10' to place the opened nozzle 94' over an aliquot tube. As depicted in FIG. 24, base 82' of container 12' is then pushed upward (suitably by a mandrel inserted in projection 92'), again shortening closure bellows 90' and increasing the pressure in container 12', as shown by the line graph of FIG. 24. This expels liquid from container 12' through nozzle 94' into aliquot tube 87, as is also shown in FIG. 17. Then motion is reversed (FIG. 25) and base 82' of container 12' is pulled down, increasing the intra-container volume of container 12', shortening closure bellows 90' and decreasing the pressure in container 12', as shown by the line graph of FIG. 25. This draws air into nozzle 94', sweeping liquid from the nozzle. Nozzle 94' is thereby sealed, as reflected in FIG. 26.

Open nozzle 94' is then repositioned in line with the laser beam or air pencil axis. Exemplifying by use of a laser beam, the laser shutter is moved out of the laser beam path, and the laser is powered up. The laser lens is not placed in the path of the laser beam. With the shutter open, the laser emits a beam onto nozzle 94'. This time the laser beam is unfocused and strikes the tip periphery of nozzle 94 as an unfocused column, melting the nozzle tip periphery. The lens shutter is then closed for a fraction of a second and reopened. The cessation of beam energy while the shutter is closed allows the nozzle tip melt to flow across the tip opening. The second burst of energy fuses the closure shut. After about another fraction of a second, the lens shutter is then closed again.

If the results of the sampling and testing by the first testing facility are questioned or challenged, containers 12 and 12' (at least one will still contain a sealed specimen therein) may be separated by severing serpentine connectors 56 and 56', and by gently rotating and/or rocking containers 12 and 12' relative to one another. The force this requires is more than a specimen vessel assembly would normally experience in normal handling but is slight enough to easily decouple the containers at members 58 and 60. Then, container 12 with a liquid specimen contained therein is sent to another testing lab to confirm the results of the first tests. At the second testing lab, tamper evident tape 100 is removed from closure 80 of container 12, and liquid specimen is withdrawn from container 12 by way of one of the nozzles 94 as described herein.

As mentioned above, the term "adjacent" is intended to include not only an embodiment in which the end of projection 92 approaches near but does not contact the upperside of floor 14, as described in the method of operation just explained, but also the term includes an embodiment in which the end of projection 92 contacts the upperside of floor 14. In that aspect of this invention, the method of this invention actuates vessel 10, after the above described steps (1) and (2), by:

(3) inverting closed container 12 not later than just before step (7) described below, that is, suitably before any one of steps (4)–(7) described below, preferably before step (4);

(4) advancing projection 92 against container floor 14 while maintaining the container stationary to extend flexure sidewall 32 of container 12, thereby enlarging the volume within container 12 and reducing the intra-container pressure;

(5) while maintaining the sidewall extension imparted in step (4), creating an aperture in nozzle 94 remote from the opening 95 thereof, for example, at the nozzle tip, thereby to equilibrate the intrachamber pressure of container 12 with ambient pressure;

(6) removing the projection 92 from contact with the container floor 14 to reduce the extension of at least flexure sidewalls 32 of container 12 sufficiently thereby to decrease the volume within container 12 and increase the intra-container pressure without forcing any liquid from container 12 through the created aperture; and (7) advancing projection 92 of the inverted container toward floor 14 thereof while maintaining the inverted container stationary, to extend flexure sidewall 90 of the closure, without contacting inverted container floor 14 with the closure projection 92, sufficiently to further decrease the volume of the inverted container and further increase the intra-container pressure to an extent effective to expel liquid from the inverted container through the aperture.

Also in the aspect of the invention where by the term "adjacent" closure projection 92 means in contact with floor 14, the method of handling a liquid sample suitably may comprise, after the primary steps (1) and (2), and (3) not later than before step (6), inverting container 12 and:

(4) advancing projection 92 against container floor 14 while maintaining container 12 stationary to extend flexure sidewall 32 of container 12, thereby enlarging the volume within container 12 and reducing the intra-container pressure;

(5) while maintaining the sidewall extension imparted in step (4), creating an aperture in nozzle 94 remote from the opening 95 thereof, for example at the tip of nozzle 94, thereby to equilibrate the intrachamber pressure of container 12 with ambient pressure; and (6) moving container floor 14 in the direction of the closure base 82 to reduce the extension of the flexure sidewalls 32 of container 12 and 90 of closure 80 sufficiently thereby to decrease the volume within the container and increase the intra-container pressure to an extent effective to expel liquid from the inverted container through the aperture.

More particularly, in the latter instance, negative intra-container pressure relative to the ambient pressure is induced in container 12' by increasing the volume of container 12'. As depicted by arrow 77 in FIG. 16, this is accomplished by pushing closure base 82' toward floor 14' of container 12'. The vertically moveable or bellows portion 90' of closure 80' is extended by the push against base 82', allowing projection 92' already in contact with floor 14' to move floor 14' away from base 82' by extending the vertically moveable or bellows sidewall portion 32'. Any air entrapped in container 12' as at 104 is not materially compressed, because projection 92 already extends to floor 14' when base 82' is pushed. Thus movement of base 82' increases the volume of container 12', and because container 12' is sealed, a negative intra-container pressure is induced relative to the ambient pressure. Movement of floor 14' of container 12' at the same time pushes coupled floor 14 of container 12 toward base 82 of container 12. This push compresses vertically moveable or bellows portion 90 of closure 80 and vertically moveable or bellows sidewall portion 32 of container 12 and reduces the volume in container 12. Any air entrapped in container 12 at 102 is compressed, and the volume of container 12 is decreased, increasing the intra-chamber pressure in container 12. The stiffness of base 82 is sufficient to assure that nozzles 94 are maintained in a substantially vertical orientation for ease of opening.

With the negative pressure induced in container 12' maintained, a nozzle 94' is opened, preferably non-invasively as with the laser system or pencil column of heated air described above. After the nozzle is opened an aliquot tube 87 is placed under the opened nozzle 94', either by moving the aliquot tube 10 under the nozzle or by rotating the vessel assembly 10 to place the opened nozzle 94 over an aliquot tube. At the same time pressure is maintained or increased on closure base 82' of container 12', assuring that no sufficiently inadvertent distance closing movement occurs during location of the aliquot tube under the nozzle that could possibly reduce volume in container 12' to expel some liquid from the container. Thus the bellows 32' and 90' of container 12' also provide the benefit of means for reduction of specimen cross contamination with other specimen specimens even with the nozzle tip open and pointing vertically downward.

Closure 80 of container 12 is then pushed downwardly toward container 12', as indicated by the arrow 79 in FIG. 17. With bellows 32' and 90' of container 12 already compressed or preloaded, pushing closure 80 toward container 12' moves projection 92 of container 12 and thereby floor 14 of container 12, thereby moving coupled floor 12' and compressing bellows 32' and 90' of container 12'. This reduces the volume of container 12'. The liquid specimen in the container is incompressible. The extent of movement of floor 14 is sufficient relative to the volume of liquid in the container to expel a volume of liquid from the container through the opened nozzle tip, as depicted in FIG. 17.

The foregoing has set forth preferred embodiments of practicing my invention, and persons of ordinary skill in the art will appreciate other embodiments which will nonetheless be within the spirit and scope of my invention, which is not intended limited to these embodiments but to be defined by the appended claims.

I claim:

1. A liquid vessel, comprising:
   (a) a container including a stiff floor, a sidewall connected at a lower portion of the sidewall to the floor and having an upper portion including a rim surrounding an opening into the container, said sidewall further including a flexure portion below said upper portion thereof,
   (b) a closure for said container, said closure including a stiff base smaller than said opening and a sidewall connected at a lower portion of the sidewall to the base, said sidewall including a flexure portion, said base having a topside and a bottomside, said bottomside including a dependent stiff projection of length to extend adjacent said container floor upon closure of said container, said topside including at least one upstanding nozzle opening only to said bottomside.

2. An assembly of the liquid vessel of claim 1 comprising a first said container and closure, a second said container and closure, and a retainer interconnecting said first and second containers, at least a portion of the retainer fixing the containers side-by-side.

3. The liquid vessel assembly of claim 2, each said container floor having an upperside and an underside, the floor of one container having on the underside thereof one member of a coupling interlock pair and the floor of the other container having on the underside thereof the other member of a coupling interlock pair.

4. The liquid vessel assembly of claim 2 in which said fixing portion of said retainer is severable.

5. The liquid vessel assembly of claim 4 in which in addition to said fixing portion said retainer comprises at least one connector loosely connecting the first and second containers.

6. The liquid vessel assembly of claim 2 further comprising a funnel for connection thereto, said funnel including a wall tapering inwardly from an upper entrance opening to two lower outlets positioned below said funnel opening, said funnel between said entrance opening and said outlets having a distributor for distributing to both said outlets a liquid admitted through the funnel entrance opening, said fixing portion of said retainer including one member of at least one pair of companion means for releasably connecting said funnel to said fixing portion in position to empty liquid from said funnel outlets into said container openings in the absence of said container closures, said funnel exteriorly of said funnel wall having the other member of said companion means for releasable connection of said funnel to said fixing portion of said retainer.

7. The liquid vessel assembly of claim 6, wherein the funnel includes a handle extending in substantially the direction of a line connecting the axes of the funnel outlets.

8. The liquid vessel of claim 1 further comprising means on said closure operative with means on said container for sealingly securing said closure to said container.

9. The liquid vessel of claim 8, wherein said closure upper portion includes a rim surrounding said opening and said closure sidewall includes an upper portion comprising a flange radially extending thereby to press on said rim of said container when said closure closes said container.

10. The liquid vessel of claim 9 in which at least the upper portion of said sidewall of said container comprises a deformable material and said rim of said container comprises a gasket, said fixing portion of said retainer includes an upright portion surrounding an upper portion of the container between said rim and said flexure portion of said sidewall, said upright portion supports said rim and has threads formed exteriorly thereon, and said closure includes a depending flange having threads formed thereon cooperative with the threads on said retainer.

11. The liquid vessel of claim 9 in which at least the upper portion of said sidewall of said container comprises a rigid material having threads formed exteriorly thereon and said closure includes a downflange having threads formed thereon cooperative with the exterior threads on said container to secure said closure to said container.

12. The liquid vessel of claim 8 in which the fixing portion of said retainer includes a ratchet reverse turn stop and said closure includes a ratchet member slideable over said stop in the forward turn direction only, said forward turn direction being the direction in which said closure is turned to screw said closure by said threads onto said container.

13. A method of handling a liquid sample, comprising:
(a) placing a specimen of a liquid in a container including a stiff floor having an upperside and bottomside, a sidewall connected at a lower portion of the sidewall to the floor, and an upper portion having a rim surrounding an opening into the container, said sidewall further having a flexure portion below said upper portion thereof, and
(b) closing the container with a closure comprising a stiff base smaller than said opening of the container and a sidewall connected to said base at a lower portion of the sidewall, said closure sidewall having a flexure portion, said closure base having a topside and a bottomside, said closure base bottomside including a dependent stiff projection of length to extend adjacent said container floor upperside upon closure of said container, and said closure base topside including at least one upstanding nozzle opening only to said closure base bottomside, whereby said closure base bottomside projection is positioned adjacent said container floor upperside.

14. The method of claim 13 in which said adjacent closure projection does not contact said container floor, and which further comprises:
(c) after step (b) and before any of steps (d)–(g), inverting the container,
(d) advancing the projection of the closure base in the closed container sufficiently toward the container floor while maintaining the container stationary, initially to extend said flexure sidewalls of the closure and push said projection of the closure base of the container into contact with the upperside of the container floor, then to extend said flexure sidewalls of the container, thereby enlarging the volume within the container and reducing the intra-container pressure,
(e) while maintaining the sidewall extensions imparted in step (d), creating an aperture in said nozzle remote from said opening thereof, thereby to equilibrate the intrachamber pressure of the container with ambient pressure,
(f) moving the projection of the closure base of the closed container in a direction away from contact with said container floor sufficiently to reduce the extension of said flexure sidewalls of the closure and the container and thereby decrease the volume within the container and increase the intra-container pressure without forcing any liquid from said container through said aperture, and
(g) advancing the projection of the closure base of the inverted container toward the floor thereof while maintaining the inverted container stationary, to extend said flexure sidewall of the closure, without contacting the inverted container floor with such closure projection, sufficiently to further decrease the volume of the inverted container and further increase the intra-container pressure to an extent effective to expel liquid from the inverted container through said aperture.

15. The method of claim 13 in which said adjacent closure projection contacts said container floor, and which further comprises:
(c) after step (b) and before any of steps (d)–(g), inverting the container,
(d) advancing the projection of the closure base in the closed container against the container floor while maintaining the container stationary to extend said flexure sidewall of the container, thereby enlarging the volume within the container and reducing the intra-container pressure, (e) while maintaining the sidewall extension imparted in step (d), creating an aperture in said nozzle remote from said opening thereof, thereby to equilibrate the intrachamber pressure of the container with ambient pressure, (f) removing the projection of the closure base of the closed container from contact with said container floor to reduce the extension of said flexure sidewalls of at least the container sufficiently thereby to decrease the volume within the container and increase the intra-container pressure without forcing any liquid from said container through said aperture, and (g) advancing the projection of the closure base of the inverted container toward the floor thereof while maintaining the inverted container stationary, to extend said flexure sidewall of the closure, without contacting the inverted container floor with such closure projection, sufficiently to further decrease the volume of the inverted container and further increase the intra-container pressure to an extent effective to expel liquid from the inverted container through said aperture.

16. The method of claim 13 in which said closure projection contacts said container floor, and which further comprises:

(c) after step (b) and before any of steps (d)–(f), inverting the container, (d) advancing the projection of the closure base in the closed container against the container floor while maintaining the container stationary to extend said flexure sidewall of the container, thereby enlarging the volume within the container and reducing the intra-container pressure, (e) while maintaining the sidewall extension imparted in step (d), creating an aperture in said nozzle remote from said opening thereof, thereby to equilibrate the intrachamber pressure of the container with ambient pressure, (f) moving said container floor in the direction of said closure base to reduce the extension of said flexure sidewalls of the container and the closure sufficiently thereby to decrease the volume within the container and increase the intra-container pressure to an extent effective to expel liquid from the inverted container through said aperture.

17. The method of any of claims 13 in which a first said container is fixed by a retainer side by side with a second like container and comprising in step (a) placing a specimen in each of such containers, and in step (b) closing each of the containers with a like said closure.

18. The method of claim 17 in which said step (a) includes placing said specimen into an entrance opening of a funnel releasably connected to said retainer, said funnel including a wall tapering inwardly from said upper entrance opening to two lower outlets positioned below said funnel opening, said funnel between said entrance opening and said outlets having a distributor for distributing said specimen to both said outlets, and further comprising, after step (a) and before step (b), disconnecting said funnel from said retainer.

19. The method of claim 17 in which said retainer includes a severable segment interconnecting said first and second containers, the floor of the first container having on the underside thereof one member of a coupling interlock pair and the floor of the second container having on the underside thereof the other member of a coupling interlock pair, and further comprising:

severing said severable segment to release the first and second containers from said fixed side-by-side position, and coupling said members of said coupling interlock pair, so that the floor of the second containers is connected to the floor of the first container and is inverted when the first container is upright.

20. The method of claims 17 in which said adjacent projection of the closure in said second container does not contact said second container floor, and which further comprises:

(c) after step (b) and before any of steps (d)–(g), inverting said second container, (d) advancing the projection of the closure base in said second container sufficiently toward the second container floor while maintaining such second container stationary, initially to extend said flexure sidewalls of the closure thereof and push said projection of the closure base of such second container into contact with the upperside of said container floor, then to extend said flexure sidewalls of such second container, thereby enlarging the volume within such second container and reducing the intra-container pressure, (e) while maintaining the sidewall extensions imparted in step (d), creating an aperture in the nozzle of such second container remote from said opening of said nozzle, thereby to equilibrate the intrachamber pressure of such second container with ambient pressure, (f) moving the projection of the closure base of such second container in a direction away from contact with said second container floor sufficiently to reduce the extension of said flexure sidewalls of the closure of the second container and such second container and thereby decrease the volume within such second container and increase the intra-container pressure without forcing any liquid from such second container through said aperture, and (g) advancing the projection of the closure base of the inverted such second container toward the floor thereof while maintaining such inverted second container stationary, to extend said flexure sidewall of the closure thereof, without contacting the inverted second container floor with such closure projection, sufficiently to further decrease the volume of such inverted second container and further increase the intra-container pressure to an extent effective to expel liquid from such inverted second container through said aperture.

21. The method of claim 20 in which said retainer includes a severable segment interconnecting said first and second containers, the floor of the first container having on the underside thereof one member of a coupling interlock pair and the floor of the second container having on the underside thereof the other member of a coupling interlock pair, and in which said step (c) is performed before step (d) and further comprises:

severing said severable segment to release the first and second containers from said fixed side-by-side position, and coupling said members of said coupling interlock pair, so that the floor of the second containers is connected to the floor of the first container and is inverted when the first container is upright.

22. The method of claim 20 further comprising sealing the opened nozzle of said inverted second container after step (g).

23. The method of claim 22 comprising, after said step of sealing, decoupling said members of said coupling pair to separate said first and second containers.

24. The method of claim 23 in which said retainer further comprises at least one serpentine connector loosely connecting the containers, and wherein said method further comprises severing said serpentine connector after said step of sealing or after said step of decoupling.

25. The method of claim 17 in which said adjacent projection of the closure in said second container contacts said second container floor, and which further comprises:

(c) after step (b) and before any of steps (d)–(g), inverting the second container, (d) advancing the projection of the closure base in the second container against the second container floor while maintaining the second container stationary to extend said flexure sidewall of the second container, thereby enlarging the volume within the second container and reducing the intra-container pressure, (e) while maintaining the sidewall extension imparted in step (d), creating an aperture in said nozzle of the second container remote from said opening of such nozzle, thereby to equilibrate the intrachamber pressure of the second container with ambient pressure, (f) removing the projection of the closure base of the second container from contact with said second container floor to reduce the extension of at least said flexure sidewalls of the second container sufficiently thereby to decrease the volume within the second container and increase the intra-container pressure thereof without forcing any liquid from said second container through said aperture, and (g) advancing the projection of the closure base of the inverted second container toward the floor thereof while maintaining the inverted second container stationary, to extend said flexure sidewall of the closure thereof, without contacting the inverted second container floor with such closure projection, sufficiently to further decrease the volume of the inverted second container and further increase the intra-container pressure to an extent effective to expel liquid from the inverted second container through said aperture.

26. The method of claim 25 in which said retainer includes a severable segment interconnecting said first and second containers, the floor of the first container having on the underside thereof one member of a coupling interlock pair and the floor of the second container having on the underside thereof the other member of a coupling interlock pair, and in which said step (c) is performed before step (d) and further comprises:

severing said severable segment to release the first and second containers from said fixed side-by-side position, and coupling said members of said coupling interlock pair, so that the floor of the second containers is connected to the floor of the first container and is inverted when the first container is upright.

27. The method of claim 25 further comprising sealing the opened nozzle of said inverted second container after step (g).

28. The method of claim 27 comprising, after said step of sealing, decoupling said members of said coupling pair to separate said first and second containers.

29. The method of claim 28 in which said retainer further comprises at least one serpentine connector loosely connecting the containers, and wherein said method further comprises severing said serpentine connector after said step of sealing or after said step of decoupling.

30. The method of claim 17 in which said adjacent projection of the closure in said second container contacts said second container floor, and which further comprises:

(c) after step (b) and before any of steps (d)–(f), inverting the second container, (d) advancing the projection of the closure base in the second container against the second container floor while maintaining the second container stationary to extend said flexure sidewall of the second container, thereby enlarging the volume within the second container and reducing the intra-container pressure, (e) while maintaining the sidewall extension imparted in step (d), creating an aperture in said nozzle of the second container remote from said opening of such nozzle, thereby to equilibrate the intrachamber pressure of the second container with ambient pressure, (f) moving the inverted second container floor in the direction of said closure base thereof to reduce the extension of said flexure sidewalls of the inverted second container and the closure thereof sufficiently thereby to decrease the volume within the inverted second container and increase the intra-container pressure to an extent effective to expel liquid from the inverted second container through said aperture.

31. The method of claim 30 in which said retainer includes a severable segment interconnecting said first and second containers, the floor of the first container having on the underside thereof one member of a coupling interlock pair and the floor of the second container having on the underside thereof the other member of a coupling interlock pair, and in which said step (c) is performed before step (d) and further comprises:

severing said severable segment to release the first and second containers from said fixed side-by-side position, and coupling said members of said coupling interlock pair, so that the floor of the second containers is connected to the floor of the first container and is inverted when the first container is upright.

32. The method of claim 30 further comprising sealing the aperture of said nozzle of said inverted second container after step (f).

33. The method of claim 32 comprising, after said step of sealing, decoupling said members of said coupling pair to separate said first and second containers.

34. The method of claim 33 in which said retainer further comprises at least one serpentine connector loosely connecting the containers, and wherein said method further comprises severing said serpentine connector after said step of sealing or after said step of decoupling.

* * * * *